(12) United States Patent
Gillberg et al.

(10) Patent No.: US 11,549,878 B2
(45) Date of Patent: Jan. 10, 2023

(54) IN VITRO METHOD FOR DETERMINING THE ADSORBING CAPACITY OF AN INSOLUBLE ADSORBANT

(71) Applicant: Albireo AB, Gothenburg (SE)

(72) Inventors: Per-Göran Gillberg, Mölndal (SE); Anna-Maria Tivert, Gothenburg (SE); Mike Frodsham, Flintshire (GB); Jamie Farrar, Flintshire (GB)

(73) Assignee: Albireo AB, Gothenburg (SE)

( * ) Notice: Subject to any disclaimer, the term of this patent is extended or adjusted under 35 U.S.C. 154(b) by 777 days.

(21) Appl. No.: 16/537,368

(22) Filed: Aug. 9, 2019

(65) Prior Publication Data

US 2020/0049611 A1 Feb. 13, 2020

Related U.S. Application Data (60) Provisional application No. 62/716,523, filed on Aug. 9, 2018.

(51) Int. Cl.
*G01N 15/08* (2006.01)

(52) U.S. Cl.
CPC . *G01N 15/0806* (2013.01); *G01N 2015/0866* (2013.01)

(58) Field of Classification Search
CPC ....... G01N 15/0806; G01N 2015/0866; G01N 33/15; A61K 9/1635; A61K 9/2846; A61K 9/2027; A61K 9/5138; A61K 9/5026; A61K 9/5036; A61K 31/74; A61K 31/745; A61K 31/787; A61K 31/785

USPC .................................................. 356/432–440
See application file for complete search history.

(56) References Cited

U.S. PATENT DOCUMENTS

| | | | |
|---|---|---|---|
| 3,539,380 | A | 11/1970 | Johnson |
| 4,172,120 | A | 10/1979 | Todd et al. |
| 4,507,235 | A | 3/1985 | Wunsch |
| 5,049,394 | A | 9/1991 | Howard et al. |
| 5,167,965 | A | 12/1992 | Schulz |
| 5,294,448 | A | 3/1994 | Ring |
| 5,350,584 | A | 9/1994 | McClelland |
| 5,422,124 | A | 6/1995 | Valducci |
| 5,578,316 | A | 11/1996 | Bhardwaj et al. |
| 5,663,165 | A | 9/1997 | Brieaddy |
| 5,681,584 | A | 10/1997 | Savastano |

(Continued)

FOREIGN PATENT DOCUMENTS

| | | |
|---|---|---|
| CA | 2065151 | 3/1991 |
| CN | 102525943 | 7/2012 |

(Continued)

OTHER PUBLICATIONS

Alvarez, "Development of crystallization processes for pharmaceutical applications," LACCEI, 2007, 2E.3-1-2E.3-9.

(Continued)

*Primary Examiner* — Hoa Q Pham
(74) *Attorney, Agent, or Firm* — Fish & Richardson P.C.

(57) ABSTRACT

The invention relates to an in vitro method for determining the adsorbing capacity of an adsorbent having limited solubility, such as a bile acid sequestrant, under conditions simulating the mammalian gastrointestinal tract. The method is particularly useful for studying the release profiles of controlled release formulations comprising adsorbents having limited solubility.

24 Claims, 3 Drawing Sheets

(56) References Cited

U.S. PATENT DOCUMENTS

| | | |
|---|---|---|
| 5,723,458 A | 3/1998 | Brieaddy et al. |
| 5,811,388 A | 9/1998 | Friend et al. |
| 5,817,652 A | 10/1998 | Brieaddy et al. |
| 5,900,233 A | 5/1999 | Day |
| 5,910,494 A | 6/1999 | Brieaddy |
| 5,976,811 A | 11/1999 | Mullner et al. |
| 5,994,391 A | 11/1999 | Lee et al. |
| 5,998,400 A | 12/1999 | Brieaddy et al. |
| 6,020,330 A | 2/2000 | Enhsen et al. |
| 6,069,167 A | 5/2000 | Sokol |
| 6,277,831 B1 | 8/2001 | Frick et al. |
| 6,346,527 B1 | 2/2002 | Takanaka et al. |
| 6,355,672 B1 | 3/2002 | Yasuma et al. |
| 6,387,924 B2 | 5/2002 | Lee et al. |
| 6,387,944 B1 | 5/2002 | Frick et al. |
| 6,426,340 B1 | 7/2002 | Gibson et al. |
| 6,562,860 B1 | 5/2003 | Keller et al. |
| 6,592,900 B1 | 7/2003 | Buhler |
| 6,635,280 B2 | 10/2003 | Shell et al. |
| 6,642,269 B2 | 11/2003 | Frick et al. |
| 6,676,979 B2 | 1/2004 | Marlett et al. |
| 6,784,201 B2 | 8/2004 | Lee et al. |
| 6,906,058 B2 | 6/2005 | Starke et al. |
| 6,943,189 B2 | 9/2005 | Keller et al. |
| 7,019,023 B2 | 3/2006 | Frick et al. |
| 7,125,864 B2 | 10/2006 | Starke et al. |
| 7,132,416 B2 | 11/2006 | Starke et al. |
| 7,132,557 B2 | 11/2006 | Wilkes et al. |
| 7,192,945 B2 | 3/2007 | Starke et al. |
| 7,192,946 B2 | 3/2007 | Starke et al. |
| 7,192,947 B2 | 3/2007 | Starke et al. |
| 7,226,943 B2 | 6/2007 | Starke et al. |
| 7,238,684 B2 | 7/2007 | Starke et al. |
| 7,514,421 B2 | 4/2009 | Abrahamsson et al. |
| 7,615,536 B2 | 11/2009 | Frick et al. |
| 7,767,229 B1 | 8/2010 | Milne et al. |
| 7,923,468 B2 | 4/2011 | Frick et al. |
| 7,939,061 B2 | 5/2011 | Prakash et al. |
| 7,956,085 B2 | 6/2011 | Frick et al. |
| 8,048,413 B2 | 11/2011 | Huguet |
| 8,067,584 B2 | 11/2011 | Starke et al. |
| 8,101,583 B2 | 1/2012 | Glombik et al. |
| 8,106,023 B2 | 1/2012 | Glombik et al. |
| 9,023,368 B2 | 5/2015 | Basit et al. |
| 9,295,677 B2 | 3/2016 | Ling et al. |
| 9,339,480 B2 | 5/2016 | Young et al. |
| 9,409,875 B2 | 8/2016 | Bohlin et al. |
| 9,684,018 B2 | 6/2017 | Horanzy |
| 9,694,018 B1 | 7/2017 | Gillberg et al. |
| 9,701,649 B2 | 7/2017 | Bohlin et al. |
| 9,745,276 B2 | 8/2017 | Bohlin et al. |
| 9,872,844 B2 | 1/2018 | Zernel et al. |
| 10,408,735 B2 * | 9/2019 | Hayden ............. G01N 15/1475 |
| 11,007,142 B2 | 5/2021 | Gillberg et al. |
| 2002/0054903 A1 | 5/2002 | Tyler et al. |
| 2002/0142054 A1 | 10/2002 | Marlett et al. |
| 2003/0124088 A1 | 7/2003 | Masuda et al. |
| 2003/0125316 A1 | 7/2003 | Keller et al. |
| 2003/0143183 A1 | 7/2003 | Knudsen et al. |
| 2003/0153541 A1 | 8/2003 | Dudley et al. |
| 2003/0153607 A1 | 8/2003 | Glinecke |
| 2003/0199515 A1 | 10/2003 | Mudipalli et al. |
| 2003/0215843 A1 | 11/2003 | Poupon et al. |
| 2004/0014806 A1 | 1/2004 | Bhat et al. |
| 2004/0038862 A1 | 2/2004 | Goodwin et al. |
| 2004/0062745 A1 | 4/2004 | Green et al. |
| 2004/0067593 A1 * | 4/2004 | Winyard ............. G01N 33/493 436/63 |
| 2004/0067933 A1 | 4/2004 | Starke et al. |
| 2004/0077625 A1 | 4/2004 | Tremont et al. |
| 2004/0082647 A1 | 4/2004 | Babiak et al. |
| 2004/0176438 A1 | 9/2004 | Tremont et al. |
| 2005/0009805 A1 | 1/2005 | Sasahara et al. |
| 2005/0089572 A1 | 4/2005 | Kumar |
| 2005/0113362 A1 | 5/2005 | Lindstedt et al. |
| 2005/0118326 A1 | 6/2005 | Anfinsen |
| 2005/0124557 A1 | 6/2005 | Lindqvist |
| 2005/0171204 A1 | 8/2005 | Lindstedt et al. |
| 2005/0197376 A1 | 9/2005 | Kayakiri et al. |
| 2005/0215882 A1 | 9/2005 | Chenevert et al. |
| 2005/0266080 A1 | 12/2005 | Desai et al. |
| 2005/0282822 A1 | 12/2005 | Alstermark et al. |
| 2006/0083790 A1 | 4/2006 | Anderberg et al. |
| 2006/0210631 A1 | 9/2006 | Patel |
| 2006/0210633 A1 | 9/2006 | Dharmadhikari |
| 2007/0197522 A1 | 8/2007 | Edwards et al. |
| 2007/0237818 A1 | 10/2007 | Malcom et al. |
| 2008/0193543 A1 | 8/2008 | Morello |
| 2008/0207592 A1 | 8/2008 | Frick et al. |
| 2008/0300171 A1 | 12/2008 | Balkan et al. |
| 2009/0098200 A1 | 4/2009 | Temtsin Krayz et al. |
| 2009/0131395 A1 | 5/2009 | Antonelli et al. |
| 2010/0130472 A1 | 5/2010 | Young et al. |
| 2010/0286122 A1 | 11/2010 | Belyk |
| 2010/0316722 A1 | 12/2010 | Lopez-Belmonte Encina et al. |
| 2011/0003782 A1 | 1/2011 | Pellicciari |
| 2011/0152204 A1 | 6/2011 | Gedulin et al. |
| 2011/0159087 A1 | 6/2011 | Sathe et al. |
| 2011/0294767 A1 | 12/2011 | Gedulin et al. |
| 2012/0114588 A1 | 5/2012 | Starke et al. |
| 2012/0157399 A1 | 6/2012 | Young et al. |
| 2013/0029938 A1 | 1/2013 | Aquino et al. |
| 2013/0052269 A1 | 2/2013 | Lescure |
| 2013/0059807 A1 | 3/2013 | Gedulin et al. |
| 2013/0108573 A1 | 5/2013 | Gedulin et al. |
| 2013/0109671 A1 | 5/2013 | Gedulin et al. |
| 2013/0225511 A1 | 8/2013 | Gillberg et al. |
| 2013/0236541 A1 | 9/2013 | Gillberg et al. |
| 2015/0031636 A1 | 1/2015 | Gillberg et al. |
| 2015/0031637 A1 | 1/2015 | Gillberg et al. |
| 2016/0039777 A1 | 2/2016 | Bohlin et al. |
| 2016/0113953 A1 | 4/2016 | Gannedahl |
| 2016/0146715 A1 | 5/2016 | Shim et al. |
| 2016/0193277 A1 | 7/2016 | Gillberg et al. |
| 2016/0194353 A1 | 7/2016 | Gillberg et al. |
| 2016/0229822 A1 | 8/2016 | Bohlin |
| 2016/0237049 A1 | 8/2016 | Bohlin |
| 2017/0143738 A1 | 5/2017 | Ando et al. |
| 2017/0143783 A1 | 5/2017 | Ando et al. |
| 2017/0182115 A1 | 6/2017 | Gillberg et al. |
| 2017/0224719 A1 | 8/2017 | Gillberg et al. |
| 2017/0224720 A1 | 8/2017 | Gillberg et al. |
| 2017/0224721 A1 | 8/2017 | Gillberg et al. |
| 2017/0240516 A1 | 8/2017 | Ymen et al. |
| 2018/0022776 A1 | 1/2018 | Gillberg et al. |
| 2018/0030088 A1 | 2/2018 | Gillberg et al. |
| 2018/0030089 A1 | 2/2018 | Gillberg et al. |
| 2018/0140219 A1 | 5/2018 | Yin et al. |
| 2018/0030009 A1 | 6/2018 | Gillberg et al. |
| 2018/0264029 A1 | 9/2018 | Gillberg et al. |
| 2018/0264030 A1 | 9/2018 | Gillberg et al. |
| 2018/0264031 A1 | 9/2018 | Gillberg et al. |
| 2018/0360869 A1 | 12/2018 | Gillberg et al. |
| 2018/0360870 A1 | 12/2018 | Gillberg et al. |
| 2018/0360871 A1 | 12/2018 | Gillberg et al. |
| 2018/0362577 A1 | 12/2018 | Gillberg et al. |
| 2019/0046451 A1 | 2/2019 | Gillberg et al. |
| 2019/0070217 A1 | 3/2019 | Gillberg et al. |
| 2019/0177286 A1 | 6/2019 | Ymen et al. |
| 2019/0367467 A1 | 12/2019 | Gillberg et al. |
| 2020/0002299 A1 | 1/2020 | Lundqvist |
| 2020/0046635 A1 | 2/2020 | Gillberg et al. |
| 2020/0046636 A1 | 2/2020 | Gillberg et al. |
| 2020/0046757 A1 | 2/2020 | Gillberg et al. |
| 2020/0046758 A1 | 2/2020 | Gillberg et al. |

FOREIGN PATENT DOCUMENTS

| | | |
|---|---|---|
| DE | 3930168 | 3/1991 |
| DE | 19825804 | 8/2000 |
| EP | 0278464 | 8/1988 |
| EP | 0489423 | 12/1991 |
| EP | 0372542 | 10/1992 |
| EP | 0573848 | 5/1993 |

(56) References Cited

FOREIGN PATENT DOCUMENTS

| | | |
|---|---|---|
| EP | 0549967 | 7/1993 |
| EP | 0624593 | 11/1994 |
| EP | 0624594 | 11/1994 |
| EP | 0624595 | 11/1994 |
| EP | 0624596 | 11/1994 |
| EP | 0594570 | 7/1995 |
| EP | 0864582 | 9/1998 |
| EP | 1173205 | 4/2000 |
| EP | 1273307 | 1/2003 |
| EP | 1535913 | 6/2005 |
| EP | 1719768 | 11/2006 |
| EP | 2144599 | 2/2008 |
| EP | 3210977 | 8/2017 |
| GB | 1573487 | 8/1980 |
| GB | 2262888 | 7/1996 |
| JP | 2000-513028 | 10/2000 |
| JP | A-2004-516285 | 6/2004 |
| JP | B-3665055 | 6/2005 |
| JP | 2006/124695 | 5/2006 |
| JP | 2013-541584 | 11/2013 |
| JP | A-2013-542953 | 11/2013 |
| JP | H02258719 | 10/2019 |
| WO | WO 1991/03249 | 3/1991 |
| WO | WO 1993/16055 | 8/1993 |
| WO | WO 1994/00111 | 1/1994 |
| WO | WO 1994/18183 | 8/1994 |
| WO | WO 1994/18184 | 8/1994 |
| WO | WO 1996/05188 | 2/1996 |
| WO | WO 1996/08484 | 3/1996 |
| WO | WO 1996/16051 | 5/1996 |
| WO | WO 1997/33882 | 9/1997 |
| WO | WO 1998/03818 | 1/1998 |
| WO | WO 1998/07449 | 1/1998 |
| WO | WO 1998/38182 | 9/1998 |
| WO | WO 1998/40375 | 9/1998 |
| WO | WO 1998/56757 | 12/1998 |
| WO | WO 1999/01149 | 1/1999 |
| WO | WO 1999/32478 | 7/1999 |
| WO | WO 1999/35135 | 7/1999 |
| WO | WO 1999/64409 | 7/1999 |
| WO | WO 1999/64410 | 12/1999 |
| WO | WO 2000/01687 | 1/2000 |
| WO | WO 2000/38725 | 7/2000 |
| WO | WO 2000/38726 | 7/2000 |
| WO | WO 2000/38727 | 7/2000 |
| WO | WO 2000/38728 | 7/2000 |
| WO | WO 2000/38729 | 7/2000 |
| WO | WO 2000/47568 | 8/2000 |
| WO | WO 2000/61568 | 10/2000 |
| WO | WO 2000/62810 | 10/2000 |
| WO | WO 2001/34570 | 5/2001 |
| WO | WO 2001/60807 | 8/2001 |
| WO | WO 2001/66533 | 9/2001 |
| WO | WO 2001/68096 | 9/2001 |
| WO | WO 2001/68637 | 9/2001 |
| WO | WO 2002/08211 | 1/2002 |
| WO | WO 2002/09815 | 4/2002 |
| WO | WO 2002/32428 | 4/2002 |
| WO | WO 2002/50051 | 6/2002 |
| WO | WO 2002/53548 | 6/2002 |
| WO | WO 2003/020710 | 3/2003 |
| WO | WO 2003/022286 | 3/2003 |
| WO | WO 2003/022804 | 3/2003 |
| WO | WO 2003/022825 | 3/2003 |
| WO | WO 2003/022830 | 3/2003 |
| WO | WO 2003/043992 | 5/2003 |
| WO | WO 2003/051821 | 6/2003 |
| WO | WO 2003/051822 | 6/2003 |
| WO | WO 2003/061663 | 7/2003 |
| WO | WO 2003/091232 | 11/2003 |
| WO | WO 2003/106482 | 12/2003 |
| WO | WO 2004/006899 | 1/2004 |
| WO | WO 2004/056748 | 7/2004 |
| WO | WO 2004/076430 | 9/2004 |
| WO | WO 2004/020421 | 10/2004 |
| WO | WO 2004/089350 | 10/2004 |
| WO | WO 2005/082874 | 9/2005 |
| WO | WO 2007/009655 | 1/2007 |
| WO | WO 2007/009656 | 1/2007 |
| WO | WO 2008/058628 | 5/2008 |
| WO | WO 2008/058630 | 5/2008 |
| WO | WO 2008/058631 | 5/2008 |
| WO | WO 2010/062861 | 6/2010 |
| WO | WO 2010/041268 | 9/2010 |
| WO | WO 2010/140007 | 12/2010 |
| WO | WO 2011/137135 | 11/2011 |
| WO | WO 2011/150286 | 12/2011 |
| WO | WO 2012/064267 | 5/2012 |
| WO | WO 2012/064268 | 5/2012 |
| WO | WO 2013/063512 | 5/2013 |
| WO | WO 2013/063526 | 5/2013 |
| WO | WO 2013/168671 | 11/2013 |
| WO | WO 2014/174066 | 10/2014 |
| WO | WO 2014/179453 | 11/2014 |
| WO | WO 2015/193788 | 12/2015 |
| WO | WO 2017/138876 | 8/2017 |
| WO | WO 2017/138877 | 8/2017 |
| WO | WO 2017/138878 | 8/2017 |
| WO | WO 2019/032027 | 2/2019 |

OTHER PUBLICATIONS

Chauhan et al., "Pharmaceutical polymers," Encycl. Biomed. Polymers and Polymeric Biomaterials, 2016, 5929-5942.

Gao et al., "Recent developments in the crystallization process: toward the pharmaceutical industry," Engineering, 2017, 3:343-353.

International Search Report and Written Opinion in Appln. No. PCT/SE2019/050603, dated Sep. 18, 2019, 11 pages.

Kolter et al., "Structure and dry binding activity of different polymers, including Kollidon VA 64," Drug Development, 2000, 26(11): 1159-65.

Loh et al., "Overview of milling techniques for improving the solubility of poorly water-soluble drugs," Asian J Pharm Sci., 2015, 10:225-274.

Lopez et al., "Formulation approaches to pediatric oral drug delivery: benefits and limitations of current platforms," Expert Opin. DrugDeliv., 2015, 12(11):1727-1740.

Neuvonen et al., "Activated charcoal in the treatment of hypercholesterolaemia: dose-response relationships and comparison with cholestyramine," Eur J Clin Pharnnacol, 1989, 37(3):225.

Ricci, "Bridging studies in support of oral pediatric formulation development," Int. J. Pharmaceuticals, 2013, 457:323-326.

Swedish Office Action in Swedish Appln. No. 1850761-6, dated Dec. 17, 2018, 8 pages.

Swedish Office Action in Swedish Appln. No. 1850762-4, dated Dec. 27, 2018, 7 pages.

Swedish Search Report in Swedish Appln. No. 1850761-6, dated Dec. 17, 2018, 3 pages.

Swedish Search Report in Swedish Appln. No. 1850762-4, dated Dec. 27, 2018, 3 pages.

Tian et al., "Factors affecting crystallization of hydrates," J. Pharm. Pharmacol., 2010, 62:1534-1546.

Boncristani et al., Respiratory Viruses, Encyclopedia of Microbiology, 2009, 19 pages.

Chang et al., "Bile acids promote the expression of hepatitis c virus in replicon-harboring cells," Journal of Virology, Sep. 2007, 81(18):9633-9640.

Colorcon.com[online] "Achieving tablet stability with mositure management," retrived on May 28, 2021, retrieved from URL<https://www.colorcon.com/connect-with-colorcon/achieving-tablet-stability-with-moisture-management>, 4 pages.

Eisai CO., Ltd., "Results from two phase 3 clinical trials of chronic constipation treatment "GOOFICE 5 mg tablet, The Lancet Gastro & Hepat., Jul. 9, 2018, 3 pages.

Greten, "Molecular therapy for the treatment of hepatocellular carcinoma," Br. J. Cancer, 2009, 100:19-23.

Kumar et al., "Cholestatic presentation of chronic hepatitis c." Dig. Dis.Sci., 2001, 46(10):2066-2073.

(56) References Cited

OTHER PUBLICATIONS

Massei et al., "Cholestasis as a presenting feature of acute epstein-barr virus infection," The pediatric Infectious Disease J., Feb. 2001, 5 pages.
Michielsen et al., "Viral hepatitis and hepatocellular carcinoma," World Journal of Surg. Oncol, May 2005, 3(27):1-18.
Morotti et al., "Progressive Familial Intrahepatic Cholestasis (PFIC) Type 1, 2, and 3: A Review of the Liver Pathology Findings," Seminars in Liver Disease, Feb. 2011, 31(1):3-10.
Mwesigwa et al, "An investigation into moisture barrier fil coating efficacy and its revelance to drug stability in solid dosage forms," Int. J. of Pharmacies, Jan. 2016, 497:70-77.
Rancaniello, "How many viruses on earth?" Virology Blog, Sep. 2013, 6 pages.
RU Office Action in Russian Appln. No. 2018131255, dated May 19, 2020, 16 pages (with English translation).
Ryder, "Guidelines for the diagnosis and treatment of hepatocellular carcinoma (HCC) in adults," Gut, May 2003, 52:(Suppl.111):iii1-iii8.
Sterling et al., "Steatohepatitis: Risk factors and impact on disease severity in human immunodeficiency virus/hepatitis c virus coinfection," Hepatology, Apr. 2008, 47(4) 1118-1127.
Sutyagin et al., Chemistry and Physics of Polymers: Textbook.—Tomsk: TPU Publishing House, 2003, p. 132, 140-143, 151-152, 173-174 (machine translation).
Thakral et al., "Eudragit: a technology evaluation," Expert Opin. Drug Deliv., Jan. 2013, 10(1):131-149.
Trauner et al., "Inflammation-induced cholestasis," J. of Gastroenterology and Hepatology, Dec. 2001, 14:10:946-959.
Walsh et al., "Respiratory syncytial and other virus infections in persons with chronic cardiopulmonary disease," American Journal of Respiratory Critical Care Med., 1999, 160:791-795.
"A Long-Term, Open-Label Study of LUM001 With a Double-Blind, Placebo Controlled, Randomized Drug Withdrawal Period to Evaluate Safety and Efficacy in Children With Alagille Syndrome (ICONIC)," Clinical Trials.gov, Jun. 9, 2014, retrieved Oct. 3, 2014, http://clinicaltrials.gov/ct2/show/NCT0216Q782?term=LUM001&rank=7, 4 pages.
"Alagile Syndrome," Wikipedia, the free encyclopedia, posted on or about Feb. 11, 2005, retrieved Feb. 12, 2014, http://en.wikipedia.org/wiki/Alagille_syndrome, 3 pages.
"Albireo's Lead Compound in Cholestatic Liver Diseases, A4250, Projects Against Bile Acid-Mediated Cholestatic Liver Injury in Mice," Albireo Press Release, Apr. 11, 2014, 2 pages.
"An Extension Study to Evaluate the Long-Term Safety and Durability of Effect of LUM001 in the Treatment of Cholestatic Liver Disease in Subjects With Alagille Syndrome (IMAGINE)," Clinical Trials.gov, Jan. 23, 2014, retrieved on Oct. 3, 2014, http://clinicaltrials.gov/ct2/show/NCT02047318?term=LUM001&rank=3, 3 pages.
"An Extension Study to Evaluate the Long-Term Safety and Durability of Effect of LUM001 in the Treatment of Cholestatic Liver Disease in Subjects With Alagille Syndrome (IMAGINE-II)," Clincal Trials.gov, Apr. 16, 2014, retrieved on Oct. 3, 2014, http://clinicaltrials.gov/ct2/show/NCT02117713?term=LUM001&rank=2, 3 pages.
"Bowel Diversion Surgeries: Ileostomy, Colostomy, Ileoanal Reservoir and Continent Ileostomy," US Department of Health and Human Services: National Institute of Diabetes and Digestive and Kidney Diseases, Feb. 2009, retrieved on Jan. 27, 2014, http://digestive.niddk.nih.gov/ddiseases/pub/ileostomy/Bowel_Diversion_508.pdf, 4 pages.
"EASL Clinical Practice Guidelines: Management of cholestatic liver diseases," European Assoc. for the Study of the Liver, Journal of Hepatology, 2009, 51:237-267.
"Evaluation of LUM001 in the Reduction of Pruritus in Alagille Syndrome (ITCH)," Clinical Trials.gov, Feb. 5, 2014, retrieved on Oct. 3, 2014, http://clinicaltrials.gov/ct2/show/NCT02057692?term=LUM001&rank=5, 4 pages.

"IBAT inhibitor A4250 for Cholestatic Pruritus," ClinicalTrials.gov, Last updated Feb. 10, 2015, https://clinicaltrials.gov/ct2/show/NCT02360852?term=a4250&rank=1, 3 pages.
"Initiation of a Phase II Trial for A4250, the Company's Lead Compound for Cholestatic Liver Diseases and NASH," Albireo Pharma Press Release, Feb. 5, 2015, http://www.alberiopharma.com/News.aspx?PageID=1600872, 2 pages.
"Lumena Pharmaceuticals Now Dosing Patients in the INDIGO Phase 2 Clinical Trial of LUM001 in Pediatric Patients with Progressive Familial Intrahepatic Cholestasis," PR Newswire, May 9, 2014, retrieved on Oct. 3, 2014, http://www.prnewswire.com/news-releases/lumena-pharmaceuticals-now-dosing-patients-in-the-indigo-phase-2-clinical-trial-of-lum001-in-pediatric-patients-with-progressive-familial-intrahepatic-cholestasis-258609691.html, 3 pages.
"Open Label Study to Evaluate Efficacy and Long Term Safety of LUM001 in the Treatment of Cholestatic Liver Disease in Patients With Progressive Familial Intrahepatic Cholestasis (INDIGO)," Clinical Trials.gov, Feb. 5, 2014, retrieved on Oct. 3, 2014, http://clinicaltrials.gov/ct2/show/NCT02057718?term=LUM001&rank=4, 3 pages.
"Open Label Study to Evaluate Safety and Efficacy of LUM001 in Patients With Primary Sclerosing Cholangitis (CAMEO)," Clinical Trials.gov, Feb. 11, 2014, retrieved Oct. 3, 2014, http://clinicaltrials.gov/ct2/show/NCT02061540?term=LUM001&rank=6, 3 pages.
"Phase 2 Study to Evaluate LUM001 in Combination With Ursodeoxycholic Acid in Patients With Primary Biliary Cirrhosis (CLARITY)," Clinical Trials.gov, Jul. 17, 2013, retrieved Oct. 3, 2014, http://clinicaltrials.gov/ct2/show/NCT01904058?term=LUM001&rank=8, 3 pages.
"Progressive familial intrahepatic cholestasis," Wikipedia, the free encyclopedia, posted on or about Feb. 24, 2006, http://en.wikipedia.org/wiki/Progressive_familial_intrahepatic_cholestasis, 3 pages.
"Safety and Efficacy Study of LUM0001 in the Treatment of Cholestatic Liver Disease in Patients With Alagille Syndrome (IMAGO)," Clinical Trials.gov, Jul. 16, 2013, http://clinicaltrials.gov/ct2/show/NCT01903460?term=LUM001&rank=1, 3 pages.
"What is Alagille Syndrome?," European Medicines Agency, Jan. 21, 2014, retrieved on Oct. 3, 2014, http://www.ema.europa.eu/docs/en_GB/document_library/Orphan designation/2014/01/WC500159874.pdf, 6 pages.
AASLD: 2017 68th Annual Meeting of the American Association for the Study of Liver Diseases, Washington, DC, Oct. 20-24, 2017, (Abstract only).
Adams et al., "Hepascore: an accurate validated predictor of liver fibrosis in chronic hepatitis C infection," Clin. Chem. 2005, vol. 51(10), p. 1867-1873.
Alashkar et al., "Meeting Info.: 57th Annual Meeting of the AmericanSociety-of-Hematology," Orlando, FL, USA. Dec. 5-8, 2015, Amer Soc Hematol, Blood, 2015, 126(23).
Alissa et al., "Invited Review: Update on Progressive Familial Intrahepatic Cholestasis," Journal of Pediatric Gastroenterology and Nutrition, 2008, 46:241-252.
Allison et al., "Studies on mixed populations of human intestinal bacteria grown in single-stage and multistage continuous culture systems," Appl. Environ. Microbial. 1989, 55(3):672-678.
Alonso et al., "Histologic pathology of the liver in progressive familial intrahepatic cholestasis," Journal of Pediatric Gastroenterology and Nutrition, 14: 128-133, 1994.
Alvarez et al., "Reduced hepatic expression of farnesoid X receptor in hereditary cholestasis associated to mutation in ATP8B1," Hum Mol Genet, 2004, 13(20):2451-2460.
Alvarez, Fernando; "Treatments in chronic cholestasis in children." Ann. Nestlé (2008) 66 p. 127-135.
American Diabetes Association, "Management of Dyslipidemia in Adults with Diabetes," Diabetes Care, Jan. 2003, 26(1).
Anakk et al., "Bile acids activate YAP to promote liver carcinogenesis," Cell Rep., Nov. 27, 2013, 5(4):1060-1069.
Angulo et al., "Independent Predictors of Liver Fibrosis in Patients With Nonalcoholic Steatohepatitis," Hepatology, Dec. 1999, 30(6): 1356-1362.
Angulo et al., "The NAFLD fibrosis score: a noninvasive system that identifies liver fibrosis in patients with NAFLD," Hepatology, 2007, vol. 45(4), p. 846-54.

(56) References Cited

OTHER PUBLICATIONS

Angulo, "Use of ursodeoxycholic acid in patients with liver disease," Current Gastroenterology Reports, Feb. 1, 2002, 4(1):37-44.

Anzivino et al., "ABCB4 and ABCB11 mutations in intrahepatic cholestasis of pregnancy in an Italian population," Dig Liver Dis., 2013, 45(3):226-232.

Appleby et al., "Effects of conventional and a novel colonic-release bile acid sequestrant, A3384, on fibroblast growth factor 19 and bile acid metabolism in healthy volunteers and patients with bile acid diarrhoea", United Eur. Gastroent. J., vol. 5, pp. 380-388, 2017.

Arnell et al., "Follow-up in children with progressive familial intrahepatic cholestasis after partial external biliary diversion," J Pediatr Gastroenterol Nutr., 2010, 51(4):494-499.

Artursson and Karlsson, "Corresslation Between Oral Drag Absorption in Humans and Apparent Drag Permeability Coefficients in Human Intestinal Epithelial (CACO-2) Cells," Biochemical and Biophysical Research Communications, Mar. 1991, 175(3):880-885.

Attili et al., "Bile Acid-induced Liver Toxicity: Relation to the Hydrophobic-Hydrophilic Balance of Bile Acids," Medical Hypotheses, 1986, 19:57-69.

Baghdasaryan et al., "Inhibition of intestinal bile acid absorption by ASBT inhibito A4250 protects against bile acid-mediated cholestatic liver injury in mice," J. Hepatology, 2014, 60:S57.

Baghdasaryan et al., "Inhibition of intestinal bile acid absorption by ASBT inhibito A4250 protects against bile acid-mediated cholestatic liver injury in mice," Presented at the EASL Conference, London, UK, Apr. 12, 2015, http://www.albireopharma.com/News.aspx?PageID=1591817, 22 pages.

Bajor et al., "Bile acids: short and long term effects in the intestine," Scandanavian J. Gastro., 2010, 45:645-664.

Balbach et al., "Pharmaceutical evaluation of early development candidates "the 100 mg-approach"," Int J Pharm, May 4, 2004, 275(1):1-12.

Banker et al., "Modern Pharmaceutics, 3ed", Marcel Dekker, New York, 1996, pp. 451 and 596.

Baumann, U. et al., "The ileal bile acid transport inhibitor A4250 decreases pruritus and serum bile acids in cholestatic liver diseases—an ongoing multiple dose, open-label, multicenter study," Hepatology, 2017, 66(1): S91 (Abstract only).

Bavin, "Polymorphism in Process Development," Chemistry and Industry, 527-529, 1989.

Beausejour et al., "Description of two new ABCB11 mutations responsible for type 2 benign recurrent intrahepatic cholestasis in a French-Canadian family," Can J Gastroenterol., 2011, 25(6):311-314.

Beraza et al., Nor-ursodeoxycholic acid reverses hepatocyte-specific nemo-dependnt steatohepatitis. Gut, 2011: 60: 387-396.

Bhaskaran et al., "Extrusion Spheronization—A Review," International Journal of PharnnTech Research.vol. 2, No. 4, pp. 2429-2433, Oct.-Dec. 2010 (Year: 2010).

Billington et al., "Effects of bile salts on the plasma membranes of isolated rat hepatocytes," Bichem. J. 188: 321-327, 1980.

Blackmore et al., "Polymorphisms in ABCB11 and ATP8B1 Associated with Development of Severe Intrahepatic Cholestasis in Hodgkin's Lymphoma," J Clin Exp Hepatol., 2013, 3(2):159-161.

Board of Appeal of European Patent Office, Case No. T 077/08—3.3.01, dated May 24, 2011, 17 pages.

Bonge et al., "Cytostar-T Scintillating Microplate Assay for Measurement of Sodium-Dependent Bile Acid Uptake in Transfected HEK-293 Cells," Analytical Biochemistiy, 2000, 282:94-101.

Bounford. University of Birmingham. Dissertation Abstracts International, (2016) vol. 75, No. IC. Order No. AA110588329. ProQuest Dissertations & Theses.

Brunt et al., "Nonalcoholic Steatohepatitis: A Proposal for Grading and Staging the Histological Lesions," American Journal of Gastroenterology, Sep. 1999, 94(9): 2467-2474.

Brunzell and Hokanson, "Dislipidemia of Central Obesity and Insulin Resistance," Diabetes Care, 1999, 22(Suppl. 3):C10-C13.

Bull et al., "Genetic and morphological findings in progressive familial intrahepatic cholestasis (Byler disease [PFIC-1] and Byler syndrome): Evidence for Heterogeneity," Hepatology, 26: 1, 155-164, 1997.

Burrows, "Interventions for treating cholestasis in pregnancy," Cochrane Database Syst. Rev., 4:CD00493, 2001.

Byrn et al., "Pharmaceutical Solids: A Strategic Approach to Regulatory Considerations," Pharmaceutical Research, 1995, 12(7), pp. 945-954.

Byrne et al., "Missense mutations and single nucleotide polymorphisms in ABCB11 impair bile salt export pump processing and function or disrupt pre-messenger RNA splicing," Hepatology., 2009, 49(2):553-567.

Caira, "Crystalline Polymorphism of Organic Compounds," in: Topics in Current Chemistry, Jan. 1998, 198:163-208.

Camilleri, "Probiotics and irritable bowel syndrome: rationale, putative mechanisms, and evidence of clinical efficacy," Clin. Gastroenterol., 40(3):264-9, Mar. 2006.

Carulli et al, "Review article: effect of bile salt pool composition on hepatic and biliary functions," Aliment. Pharmacol. Ther. 2000, vol. 14, suppl. 2, p. 14-18.

Centeno, "Molecular mechanisms triggered by low-calcium diets," Nutrition research reviews., 22(2):163-74, Dec. 2009.

Chalasani et al., "The diagnosis and management of nonalcoholic fatty liver disease: Practice guidance from the American Association for the Study of Liver Diseases," Hepatology, 2018, 67(1):328-357.

Chen et al., "Bile salt export pump is dysregulated with altered farnesoid X receptor isoform expression in patients with hepatocelular carcinoma," Hepatologu, 57: 4, 1530-1541, 2013.

Chen et al., "Diagnosis of BSEP/ABCB11 mutations in Asian patients with cholestasis using denaturing high performance liquid chromatography," J Pediatr., 2008, 153(6):825-832.

Chen et al., "FIC1 and BSEP defects in Taiwanese patients with chronic intrahepatic cholestasis with low gamma-glutamyltranspeptidase levels," Journal of Pediatrics, 2002, 140(1):119-124.

Chen et al., "Inhibition of apical sodium-dependent bile acid transporter as a novel treatment for diabetes," Am J Physiol Endocrinol Metab, 2012, 302:E68-E76.

Chen et al., "Progressive Familial Intrahepatic Cholestasis, Type 1, is Associated with Decreased Famesoid X Receptor Activity," Gastroenterology, 2004, 126:756-764.

Chen et al., "Serum and urine metabolite profiling reveals potential biomarkers of human hepatocellular carcinoma," Molecular and Cellular Proteomics 10.7, 2011.

Chen et al., "The effects of diets enriched in beta-glucans on blood lipoprotein concentrations," J. Clin. Lipidol., 3(3):154-8, May 2009.

Chen et al., "Treatment effect of rifampicin on cholestasis," Internet Journal of Pharmacology, 4(2), 2006.

Chey et al., "A Randomized Placebo-Controlled Phase II b Trial of A3309, A Bile Acid Transporter Inhibitor, for Chronic Idiopathic Constipation," Am. J. Gastroenterology, May 2011, 106:1803-1812.

Chiang, "Bile acids: regulation of synthesis," J. Lipid Res, 2009, 50(10):1955-1966.

Chourasia et al., "Polysaccharides for colon targeted drag delivery," Drag Delivery, Academic Press, vol. 11, No. 2, Jan. 1, 2004, 129-148, XP008060983.

Copeland et al., "Novel splice-site mutation in ATP8B1 results in atypical progressive familial intrahepatic cholestasis type 1," J Gastroenterol Hepatol., 2013, 28(3):560-564.

Danese et al., "Analytical evaluation of three enzymatic assays for measuring total bile acids in plasma using a fully-automated clinical chemistry platform," PLoS One, 2017, 12(6):e0179200.

Das & Kar., Non alcoholic steatohepatitis. JAPI. 53:, Mar. 2005.

Dashti et al., "A Phospholipidomic Analysis of All Defined Human Plasma Lipoproteins," Nature.com: Scientific Reports, Nov. 2011, DOI: 10.1038, 11 pages.

Davit_Spraul et al., "ATP8B1 and ABCB11 Analysis in 62 Children with Normal Gamma-Glutamyl Transferase Progressive Familial Intrahepatic Cholestasis (PFIC): Phenotypic Differences Between PFIC1 and PFIC2 and Natural History," Hepatology: Autoimmune, Cholestatic and Biliary Disease, May 2010, 1645-1655.

(56) References Cited

OTHER PUBLICATIONS

Davit-Spraul et al., "Liver transcript analysis reveals aberrant splicing due to silent and intronic variations in the ABCB11 gene," Mol Genet Metab., 2014, 113(3):225-229.
Davit-Spraul et al., "Progressive familial intrahepatic cholestasis," Orphanet Journal of Rare Diseases, Jan. 2009, 4:1-12.
Dawson et al., "Bile acid transporters" J. Lipid Res. 2009, 50, 2340-2357.
Dawson, "Role of the intestinal bile acid transporters in bile acid and drug disposition," Handb. Exp. Pharmacol. 2011, 201:169-203.
De Lédinghen et al., "Controlled attenuation parameter for the diagnosis of steatosis in non-alcoholic fatty liver disease," J Gastroenterol Hepatol., 2016, 31(4):848-855.
DeFronzo et al., "Insuline resistance, A multisurfaced syndrome responsible for NIDDM, obesity, hypertension, dyslipidemia and atherosclerotic cardiovascular disease," Diabetes Care, 1991, 14:173-194.
Deng et al., "Novel ATP8B1 mutation in an adult male with progressive familial intrahepatic cholestasis," World J Gastroenterol., 2012, 18(44):6504-6509.
Di Lascio et al., "Steato-Score: Non-invasive Quantitative Assessment of Liver Fat by Ultrasound Imaging," Ultrasound Med Biol., 2018, 44(8):1585-1596.
Di Padova et al., "Double-blind placebo-controlled clinical trial of microporous chlestyramine in the treatment of intra- and extra-hepatic cholestasis: relationship between itching and serum bile acids," Methods Find Exp Clin Pharmacol., Dec. 1984, 6(12):773-776 (Abstract Only).
DiBaise et al., "Bile Acids: An Underrecognized and Underappreciated Cause of Chronic Diarrhea", Pract. Gastroenterol. vol. 36(10), p. 32-44, 2012.
Dixon et al., "An expanded role for heterozygous mutations of ABCB4, ABCB11, ATP8B1, ABCC2 and TJP2 in intrahepatic cholestasis of pregnancy," Scientific Reports, 2017, 7(1):11823.
Dong et al., "Structure-activity relationship for FDA approved drugs as inhibitors of the human sodium taurocholate cotransporting polypeptide (NTCP).," Mol. Pharm. 2013, 10(3):1008-1019.
Dongiovanni et al., "Genetic Predisposition in NAFLD and NASH: Impact on Severity of Liver Disease and Response to Treatment," Curren Pharma Design, 2013, 19:5219-5238.
Drage et al., "Exon-skipping and mRNA decay in human liver tissue: molecular consequences of pathogenic bile salt export pump mutations," Sci Rep., 2016, vol. 6: 24827.
Drage et al., "Sequencing of FIC1, BSEP and MDR3 in a large cohort of patients with cholestasis revealed a high number of different genetic variants," J Hepatol. 2017, 67(6):1253-1264.
Droge et al., Zeitschrift fur Gastroenterologie 2015, 53(12) Abstract No. A3-27. Meeting Info: 32. Jahrestagung der Deutschen Arbeitsgemeinschaft zum Studium der Leber. Dusseldorf, Germany. Jan. 22, 2016-Jan. 23, 2016.
Drumond et al., "Patients' appropriateness, acceptability, usability and preferences for pharmaceutical preparations: Results from a literature review on clinical evidence," Int. J. Pharm. 2017, 521(1-2):294-305.
Einspahr et al., "Protective role of wheat bran fiber: data from marker trials," Am. J. Med., 106(1A):32s-37s, Jan. 1999.
Ekkehard Sturm et al. The ileal bile acid transport inhibitor A4250 reduced pruritus and semm bile acid levels in children with cholestatic liver disease and pruritus: final results from a multiple-dose, open-label, multinational study Hepatology 2017; 66: 646-47 (Suppl. 1). doi: 10.1002/hep.29501.
Ellinger et al., "Partial external biliary diversion in bile salt export pump deficiency: Association between outcome and mutation," World J Gastroenterol., 2017, 23(29):5295-5303.
Ellis et al., "Zebrafish abcb11b mutant reveals strategies to restore bile excretion impaired by bile salt export pump deficiency," Hepatology, 2018, 67(4)1531-1545.
Engelen et al., "Oral size perception of particles: effect of size, type, viscosity and method," J. Text. Studies 2005, 36(4):373-386.

Espenshade and Hughes, "Regulation of Sterol Synthesis in Eukaryotes," Annu. Rev. Genet., 2007, 41:401-427.
Evason et al., "Morphologic findings in progressive familial intrahepatic cholestasis 2 (PFIC2): correlation with genetic and immunohistochemical studies," Am J Surg Pathol., 2011, 35(5):687-696.
Evonik Industries, "Eudragit FS 30 D," Jul. 9, 2008, http://www.pharma-polymers.com.pharmapolymers/MCMbase/Pages/ProvideResource.aspx?respath=/NR/rdonlyres/BDD7E168-922E-4AB1-861F-EEEB58B85642/0/EUDRAGITFS30D_Promotiondatasheet_09072008.
Extended European Search Report in European Application No. 11840392.2, dated Feb. 24, 2014, 7 pages.
Extended European Search Report in European Application No. 11840481.3, dated Feb. 13, 2014, 10 pages.
Faubion et al., "Toxic bile salts induce rodent hepatocyte apoptosis via direct activation of Fas," The Journal of Clinical Investigation, 103: 1, 137-145, 1999.
Ferreira et al., Pediatric Transplantation 2013, 17(Suppl. 1):99. Abstract No. 239. Meeting Info: IPTA 7th Congress on Pediatric Transplantation. Warsaw, Poland. Jul. 13, 2013-Jul. 16, 2013.
Ferslew et al., "Altered Bile Acid Metabolome in Patients with Nonalcoholic Steatohepatitis," Dig Dis Sci., 2015, 60(11):3318-3328.
Folmer et al., "Differential effects of progressive familial intrahepatic cholestasis type 1 and benign recurrent intrahepatic cholestasis type 1 mutations on canalicular localization of ATP8B1," Hepatology., 2009, 50(5):1597-1605.
Forner et al., "Treatment of hepatocellular carcinoma," Critical Reviews in Oncology/Hematology, 2006, 60:89-98.
Francalanci et al., "Progressive familial intrahepatic cholestasis: Detection of new mutations and unusal modality of transmission," Digestive and Liver Disease 2010, 42(Suppl. 1):516, Abstract No. T.N.5.
Francalanci et al., Laboratory Investigation 2011, vol. 91, Supp. Suppl. 1, p. 360A. Abstract No. 1526.
Fuentes-Zaragoza al., "Resistant Starch as functional ingredient: A review", , Food Research International, 43, 931-942, 2010.
Fuller, "Probiotics in man and animals," Appl. Bacterial. 1989, 66(5):365-378.
Gao et al., "Detection of hepatitis in children with idiopathic cholestatic bile salt export pump gene mutations," Shandong Yiyao, 2012, 52(10):14-16.
Gao et al., "The Identification of Two New ABCB11 Gene Mutations and the Treatment Outcome in a Young Adult with Benign Recurrent Intrahepatic Cholestasis: A Case Report," Hepatitis Monthly 2017, 17(10):e55087/1-e55087/6.
Gibney, "Shire Reports Topline Results from First of Three Placebo-Controlled Phase 2 Studies of SHP625 (LUM001) in Children with Alagille Syndrome," FierceBiotech.com, Apr. 9, 2015, http://www.firecebiotech.com/node/443176/print, 3 pages.
Gibson and Roberfroid, "Dietary modulation of the human colonic microbiota: introducing the concept of prebiotics," J. Nutr. 1995, 125(6):1401-1412.
Gillberg et al., "The IBAT Inhibition by A3309—A Potential Mechanism for the Treatment of Constipation," Gastroenterology, 2010, 138(5), Supp 1, S-224.
Giovannoni et al., "Genetics and Molecular Modeling of New Mutations of Familial Intrahepatic Cholestasis in a Single Italian Center," PLoS One, 2015, 10(12):e0145021.
Glagov et al., "Compensatory enlargement of human athersclerotic coronary arteries," N Engl. J. Med., May 1987, 316(22):1371-1375 (Abstract Only).
Goldschmidt et al., "Increased frequency of double and triple heterozygous gene variants in children with intrahepatic cholestasis," Hepatol Res., 2016, 46(4):306-311.
Govers et al., "Characterization of the adsorption of conjugated and unconjugated bile acids to insoluble, amorphous calcium phosphate", Journal of Lipid Research 35(5):741-748, 1994.
Griffin, et al., "A novel gene mutation in ABCB11 in siblings with progessive familial intrahepatic cholestasis type 2," Canadian Journal of Gastroenterology and Hepatology 2016, vol. 2016. Abstract (56) References Cited

OTHER PUBLICATIONS

No. A200. Meeting Info: 2016 Canadian Digestive Diseases Week, CDDW 2016. Montreal, QC, United States. Feb. 26, 2016-Feb. 29, 2016.
Gunaydin et al., "Progressive familial intrahepatic cholestasis: diagnosis, management, and treatment," Hepat Med., 2018, 10:95-104.
Guorui et al., "Genetic diagnosis of progressive familial intrahepatic cholestasis type 2," Linchuang Erke Zazhi, 2013, 31(10):905-909.
Guzman et al., "Does Nonalcoholic Fatty Liver Disease Predispose Patients to Hepatocellular Carcinoma in the Absence of Cirrhosis?" Archives of pathology & laboratory medicine, Nov. 2008, 132(11):1761-1766.
Hancock et al., "Molecular Mobility of amorphous pharmaceutical solids below their glass transition temperatures," 12(6): 799-806, 1995.
Hao et al., "Application of high-throughput sequencing technologies with target capture/target next-generation sequencing in diagnosis of neonatal intrahepatic cholestasis causes by citrin deficiency (NICDD)," International Journal of Clinical and Experimental Pathology, 2017, 10(3):3480-3487.
Harmanci et al., "Late onset drug induced cholestasis in a living-related liver transplantation donor to son with progressive familial intrahepatic cholestasis," Experimental and Clinical Transplantation 2015, 13(2):76, Abstract No. P62. Meeting Info: 1st Congress of the Turkic World Transplantation Society. Astana, Kazakhstan. May 20, 2015-May 22, 2015.
Hasegawa et al., "Intractable itch relieved by 4-phenylbutyrate therapy in patients with progressive familial intrahepatic cholestasis type 1," Orphanet J Rare Dis., 2014, 9:89.
Hayashi et al., "Assessment of ATP8B1 Deficiency in Pediatric Patients With Cholestasis Using Peripheral Blood Monocyte-Derived Macrophages," EBioMedicine, 2018, 27:187-199.
Hayashi et al., "Successful treatment with 4-phenylbutyrate in a patient with benign recurrent intrahepatic cholestasis type 2 refractory to biliary drainage and bilirubin absorption," Hepatol Res., 2016, 46(2):192-200.
Heathcote, "Management of primary biliary cirrhosis," Hepatology, 2000, 31(4):1005-1013.
hepc.liverfoundation.org' [online]. "Nonalcoholic Fatty Liver Disease," Brochure, 2016 [retrieved on Feb. 1, 2018], Retrived from the Internet: URL<http://hepc.liverfoundation.org/wp-content/uploads/2012/07/NAFLD-Brochure-2016.pdf>, 8 pages.
Herbst et al., "Taking the next step forward—Diagnosing inherited infantile cholestatic disorders with next generation sequencing," Mol Cell Probes, 2015, 29(5):291-298.
Higaki et al., "Inhibition of ileal na+/bile acid cotranporter by S-8921 reduces serum cholesteral and prevents atherosclerosis in rabbits", Arteriosclerosis, Thrombosis, and Vascular Biology 18(8):1304-1311, 1998.
Ho et al., "Polymorphic variants in the human bile salt export pump (BSEP; ABCB11): functional characterization and interindividual variability," Pharmacogenet Genomics, 2010, 20(1):45-57.
Hoffman et al., Human Anatomy, picture of the colon, p. 1-7, https://www.webmd.com/digestive-disorders/picture-of-the-colon #1, Accesses Aug. 4, 2019.
Hollands et al., "Ileal exclusion for Byler's disease: an alternative surgical approach with promising early results for pruritis,"Journal of Pediatric Surgery, Feb. 1988, 33(2): 220-224.
Holz et al., "Can genetic testing guide the therapy of cholestatic pruritus? A case of benign recurrent intrahepatic cholestasis type 2 with severe nasobiliary drainage-refractory itch," Hepatol Commun., 2018, 2(2):152-154.
Holz et al., "Plasma separation and anion adsorption results in rapid improvement of nasobiliary drainage (NBD)—refractory pruritus in BRIC type 2," Zeitschrift fur Gastroenterologie 2016, vol. 54, No. 8. Abstract No. KV275. Meeting Info: Viszeralmedizin 2016, 71. Jahrestagung der Deutschen Gesellschaft fur Gastroenterologie, Verdauungs—und Stoffwechselkrankheiten mit Sektion Endoskopie—10. Herbsttagung derDeutschen Gesellschaft fur Allgemein—und Viszeralchirurgie. Hamburg, Germany, Sep. 21, 2016-Sep. 24, 2016.
Hsu et al., "Adult progressive intrahepatic cholestasis associated with genetic variations in ATP8B1 and ABCB11," Hepatol Res., 2009, 39(6):625-631.
Hu et al., "Diagnosis of ABCB11 gene mutations in children with intrahepatic cholestasis using high resolution melting analysis and direct sequencing," Mol Med Rep., 2014, 10(3):1264-1274.
Huang et al., "Discovery of Potent, Nonsystemic Apical Sodium-Codependent Bile Acid Transporter Inhibitors (Part 2)," J. Med. Chem., 2005, 48:5853-5868.
Imagawa et al., "Clinical phenotype and molecular analysis of a homozygous ABCB11 mutation responsible for progressive infantile cholestasis," J Hum Genet. 2018, 63(5):569-577.
Imagawa et al., "Generation of a bile salt export pump deficiency model using patient-specific induced pluripotent stem cell-derived hepatocyte-like cells," Sci Rep., 2017, 7:41806.
Imagawa et al., "Splicing analysis using induced pluripotent stem cell-derived hepatocyte-like cells generated from a patient with progressive familial intrahepatic cholestatsis type 2," Journal of Pediatric Gastroenterology and Nutrition 2016, 63(2):551, Abstract No. 166, Meeting Info: World Congress of Pediatric Gastroenterology, Hepatology and Nutrition 2016. Montreal, QC, Canada. Oct. 5, 2016-Oct. 8, 2016.
International Preliminary Report on Patentability for Application No. PCT/JP2015/068240, dated Jan. 5, 2017, 12 pages (with English translation).
International Preliminary Report on Patentability for International Application No. PCT/EP2015/074573, dated Apr. 25, 2017, 8 pages.
International Preliminary Report on Patentability for International Application No. PCT/SE2011/051335, dated May 23, 2011, 7 pages.
International Preliminary Report on Patentability for International Application No. PCT/SE2011/051336, dated May 23, 2013, 11 pages.
International Search Report and Written Opinion for Application No. PCT/EP2014/058432, dated Jul. 11, 2014, 9 pages.
International Search Report and Written Opinion for Application No. PCT/SE2017/050126, dated Apr. 24, 2017, 27 pages.
International Search Report and Written Opinion for Application No. PCT/SE2017/050127, dated May 8, 2017, 16 pages.
International Search Report and Written Opinion for Application No. PCT/SE2017/050128, dated May 8, 2017, 16 pages.
International Search Report and Written Opinion for Appln. No. PCT/EP2019/064602, dated Aug. 9, 2019, 11 pages.
International Search Report and Written Opinion for International Application No. PCT/EP2015/074573, dated Apr. 28, 2016, 11 pages.
International Search Report and Written Opinion for International Application No. PCT/SE2011/051335, dated Feb. 3, 2012, 12pages.
International Search Report and Written Opinion for International Application No. PCT/SE2011/051366, dated Feb. 22, 2012, 18 pages.
International Search Report and Written Opinion in International Application No. PCT/SE2018/050802, dated Oct. 26, 2018.
International Search Report and Written Opinion in International Application No. PCT/SE2018/050803, dated Oct. 26, 2018.
International Search Report, Application No. PCT/JP2015/068240, dated Sep. 15, 2015, 11 pages (with English translation).
Ishak et al., "Histological grading and staging of chronic hepatitis," J. Hepatol. 1995, vol. 22, p. 696-699.
Ishibashi et al., "Hypercholesterolemia in low density lipoprotein receptor knockout mice and its reversal by adenovirus-mediated gene delivery", Journal of Clinical Investigation 92(2):883-893, 1993.
Islam and Di Baise, "Bile Acids: An underrecognized and under-appreciated cause of chronic diarrhea," Pract. Gastroenterol. 2012, vol. 36(10), p. 32-44.
Ivashkin et al., "A novel mutation of ATP8B1 gene in young patient with familial intrahepatic cholestasis.," Hepatology International 2016, 10(1):5461, Abstract No. LBO-38. Meeting Info: 25th Annual Conference of the Asian Pacific Association for the Study of the Liver, APASL 2016. Tokyo, Japan. Feb. 20, 2016-Feb. 24, 2016.

(56) References Cited

OTHER PUBLICATIONS

Jacobsen et al., "Effect of enterocoated cholestyramine on bowel habit after ileal resection: a double blind crossover study," Br. Med. J. 1985, vol. 290, p. 1315-1318.

Jacquet et al., "Alagille Syndrome in Adult Patients: It is Never Too Late," American Journal of Kidney Diseases, May 2007, 49(5):705-709.

Jankowska et al., "[Cholestatic liver disease in children]," Przegl. Epidemiol., 56:16-21, 2002.

Jankowska et al., "Ileal exclusion in children with progressive familial intrahepatic cholestasis," J Pediatr Gastroenterol Nutr. 2014,58(1):92-95.

Jansen et al., "Endogenous bile acids as carcinogens," Journal of Hepatology, Sep. 2007, 47(3):434-435.

Jaquotot-Haerranz et al., "Clinical variability of mutations in the ABCB11 gene: a case report," Rev Esp Enferm Dig., 2013, 105(1):52-54.

Jericho et al., "Bile Acid Pool Dynamics in Progressive Familial Intrahepatic Cholestasis with Partial External Bile Diversion," Journal of Pediatric Gastroenterology and Nutrition, 2015, 60(3):368-374.

Jiang et al., "Non alcoholic steatohepatitis a precursor for hepatocellular carcinoma development," World Journal of Gastroenterology: WJG, Nov. 28, 2014, 20(44):16464-16473.

Jirsa et al., "Indel in the FIC1/ATP8B1 gene—a novel rare type of mutation associated with benign recurrent intrahepatic cholestasis," Hepatol Res. 2004, 30(1):1-3.

Jung et al., "Prenatal molecular diagnosis of inherited cholestatic diseases," J Pediatr Gastroenterol Nutr. 2007, 44(4):453-458.

Kagawa et al., "Phenotypic differences in PFIC2 and BRIC2 correlate with protein stability of mutant Bsep and impaired taurocholate secretion in MDCK II cells," Am J Physiol Gastrointest Liver Physiol., 2008, 294(1):G58-67.

Kang et al., "Progressive Familial Intrahepatic Cholestasis in Korea: A Clinicopathological Study of Five Patients," J Pathol Transl Med. May 16, 2019, 53(4):253-260.

Karpen and Dawson, "Not all (bile acids) who wander are lost: the first report of a patient with an isolated NTCP defect," Hepatology, 2015, 61(1):24-27.

Khosla et al., "Recurrent Post-partum Jaundice: Rare Genetic Disorder With Novel Genetic Mutations Identified," American Journal of Gastroenterology 2015, 110(1):5397. Meeting Info.: 80th Annual Scientific Meeting of the American-College-of-Gastroenterology. Honolulu, HI, USA. Oct. 16-21, 2015.

Kim, "Novel mutation of ABCB 11 heterozygote associated with transient neonatal intrahepatic cholestasis," Journal of Pediatric Gastroenterology and Nutrition 2016, 62(1):620, Abstract No. H-P-045. Meeting Info: 49th Annual Meeting of the European Society for Pediatric Gastroenterology, Hepatology and Nutrition, ESPGHAN 2016. Athens, Greece. May 25, 2016-May 28, 2016.

Kleiner et al., "Design and validation of a histological scoring system for nonalcoholic fatty liver disease," Hepatology, 2005, 41(6):1313-1321.

Klomp et al., "Characterization of mutations in ATP8B1 associated with hereditary cholestasis," Hepatology, 2004, 40(1):27-38.

Knisely et al., "Hepatocellular Carcinoma in ten children under five years of age with bile salt export pump deficiency," Hepatology, Aug. 2006, 44(2):478-486.

Kooistra, et al., "KLIFS: A structural kinase-ligand interaction database," Nucleic Acids Res. 2016, 44(D1):D365-D371.

Korman et al., "Assessment of Activity in Chronic Active Liver Disease," New England Journal of Medicine, 2010, 290(25):1399-1402.

Kosters et al., "Bile acid transporters in health and disease," Xenobiotica 2008, 38(7-8):1043-1071.

Kozarewicz, "Regulatory perspectives on acceptability testing of dosage forms in children," Int. J. Pharm. 2014, 469(2):245-248.

Krawczyk et al., "Prolonged cholestasis triggered by hepatitis A virus infection and variants of the hepatocanalicular phospholipid and bile salt transporters," Ann Hepatol., 2012, 11(5):710-744.

Kumar and Tandon, "Use of ursodeoxycholic acid in liver diseases," J. Gastroenterology and Hepatology, 2001, 16:3-14.

Kurata et al., "A novel class of apical sodium-dependent bile acid transporter inhibitors: the amphiphilic 4-oxo-1-phenyl-1,4-dihydroquinoline derivatives," Bioorganic & Medicinal Chemistry Letters, 2004, 14:1183-1186.

Kurbegov et al., Biliary diversion for progressive familial intrahepatic cholestasis: Improved liver morphology and bile acid profile, Gastroenterology, 125: 4, 1227-1234, 2003.

Lam et al., "A patient with novel ABCB11 gene mutations with phenotypic transition between BRIC2 and PFIC2," J Hepatol. 2006, 44(1):240-242.

Lam et al., "Levels of plasma membrane expression in progressive and benign mutations of the bile salt export pump (Bsep/Abcb11) correlate with severity of cholestatic diseases," Am J Physiol Cell Physiol. 2007, 293(5):C1709-16.

Lang et al,. "Genetic variability, haplotype structures, and ethnic diversity of hepatic transporters MDR3 (ABCB4) and bile salt export pump (ABCB11)," Drug Metab Dispos. 2006, 34(9):1582-1599.

Lang et al., "Mutations and polymorphisms in the bile salt export pump and the multidrug resistance protein 3 associated with drug-induced liver injury," Pharmacogenet Genomics, 2007, 17(1):47-60.

Lanzini et al., "Intestinal absorption of the bile acid analogue $^{75}$Se-homocholic acid-taurine is increased in primary biliary cirrhosis and reverts to normal during ursodeoycholic acid administrations," Gut, 2003, 52:1371-1375.

Lee et al., "Early Diagnosis of ABCB11 Spectrum Liver Disorders by Next Generation Sequencing," Pediatr Gastroenterol Hepatol Nutr. 2017, 20(2):114-123.

Lewis et al., "Effects of 2164U90 on ileal bile acid adsorption and serum cholesterol in rats and mice", Journal of Lipid Research 36(5):1098-1105, 1995.

Li et al., "ATP8B1 and ABCB11 mutations in Chinese patients with normal gamma-glutamyl transferase cholestasis: Phenotypic differences between progressive familial intrahepatic cholestasis type 1 and 2," Hepatology International 2017, 11(1):5180. Abstract No. OP284.

Li et al., "Clinical feature and gene mutation analysis of one pedigree with progressive familial intrahepatic cholestasis type II," Hepatology International 2017, 11(1):5362, Abstract No. PP0347. Meeting Info: 26th Annual Conference of the Asian Pacific Association for the Study of the Liver, APASL 2017. Shanghai, China. Feb. 15, 2017-Feb. 19, 2017.

Li et al., "Effect of Resistant Starch Film Properties on the Colon-Targeting Release of Drug From Coated Pellets", 152 J Control. Rel. e5, 2011.

Lichtinghagen R, et al., "The Enhanced Liver Fibrosis (ELF) score: normal values, influence factors and proposed cut-off values," J Hepatol. Aug. 2013;59(2):236-42.

Lin et al., "[Clinical and genetic analysis of an infant with progressive familial intrahepatic cholestasis type II].," Zhongguo Dang Dai Er Ke Za Zhi. 2018, 20(9)758-764 (with English abstract).

Ling, "Congenital cholestatic syndromes: What happens when children grow up?," Can J Gastroenterol, Nov. 11, 2007, 21(11):743-751.

Liu et al., "ABCB11 gene mutations in Chinese children with progressive intrahepatic cholestasis and low gamma glutamyltransferase," Liver International 2010, 30(6):809-815.

Liu et al., "Association of variants of ABCB11 with transient neonatal cholestasis," Pediatr Int. 2013, 55(2):438-144.

Liu et al., "Characterization of ATP8B1 gene mutations and a hot-linked mutation found in Chinese children with progressive intrahepatic cholestasis and low GGT," J Pediatr Gastroenterol Nutr., 2010, 50(2):479-183.

Liu et al., "Characterization of ATP8B1 mutations and a hot linked mutation found in Chinese children with progressive intrahepatic cholestasis and low GGT," Hepatology International 2009, 3(1):184-185, Abstract No. PE405. Meeting Info: 19th Conference of the Asian Pacific Association for the Study of the Liver. Hong Kong, China. Feb. 13, 2009-Feb. 16, 2009.

(56) References Cited

OTHER PUBLICATIONS

Liu et al., "Homozygous p.Ser267Phe in SLC10A1 is associated with a new type of hypercholanemia and implications for personalized medicine," Scientific Reports, 2017, 7:9214.
Liu, et al., "Patient-centered pharmaceutical design to improve acceptability of medicines: similarities and differences in paediatric and geriatric populations," Drugs 2014, 74(16):1871-1889.
Longo et al., "Hyperlipidemia in chronic cholestatic liver disease," Curr. Treat. Options Gastrenterol., 2001, 4:111-114.
Lopez et al., "Effect of formulation variables on oral grittiness and preferences of multiparticulate formulations in adult volunteers," Eur. J. Pharm. Sci. 2016, 92:156-162.
Lv et al., "Noninvasive Quantitative Detection Methods of Liver Fat Content in Nonalcoholic Fatty Liver Disease," J Clin Transl Hepatol. 2018, 6(2):217-221.
Lykavieris et al., "Outcome of liver disease in children with Alagille syndrome: a study of 163 patients," Gut, 2001, 49:431-435.
Maggiore et al., "Relapsing features of bile salt export pump deficiency after liver transplantation in two patients with progressive familial intrahepatic cholestasis type 2," J Hepatol. 2010, 53(5):981-6.
Manghat and Wierzbicki, "Colesevelam hydrochloride: a specifically engineered bile acid sequestrant," Future Lipidology, 3(3):237-255, Jun. 2008.
Marzorati et al., "A novel hypromellose capsule, with acid resistance properties, permits the targeted delivery of acid-sensitive products to the intestine," LWT-Food Sci. Techno.l 2015, vol. 60, p. 544-551.
Masahata et al., "Recurrence of Progressive Familial Intrahepatic Cholestasis Type 2 Phenotype After Living-donor Liver Transplantation: A Case Report," Transplant Proc. 2016, 48(9):3156-3162.
Matte et al., "Analysis of gene mutations in children with cholestasis of undefined etiology," J Pediatr Gastroenterol Nutr. 2010, 51(4):488-493.
McCullough et al., "The epidemiology and risk factors of NASH.", Blackwell Publishing, Chapter 3, 2005.
McKay et al., "Mutation detection in cholestatic patients using microarray resequncing of ATP8B1 and ABCB11 [version 2; peer review: 2 approved, 1 approved with reservations]," F1000 Res., 2013, 2:32.
McMichael and Potter, "Reproduction, endogenous and exogenous sex hormones, and colon cancer: a review and hypothesis," J. Natl. Cancer Inst., 65(6):1201-07, Dec. 1980.
McPherson et al., "Simple non-invasive fibrosis scoring systems can reliably exclude advanced fibrosis in patients with non-alcoholic fatty liver disease," Gut 2010, 59(9):1265-9.
MerckManuals.com', "Obesity," 2008, Merch Manual for Health Care Professionals, Section-Nutritional Disorders, Chapter—"Obesity and the metabolic syndrome," retrieved on Feb. 22, 2012, http://www.merchmanuals.com/professional/nutritional_disorders/obesity_and_the_metabolic_syndrome/metabolic_syndrome.html?qt=metabolicsyndrome&alt=sh, 10 pages.
Miloh et al., Gastroenterology 2006, vol. 130, No. 4, Suppl. 2, pp. A759-A760. Meeting Info.: Digestive Disease Week Meeting/107th Annual Meeting of the American-GastroenterologicalAssociation. Los Angeles, CA, USA, May 19.
Minekus et al., "A computer-controlled system to simulate conditions of the large intestine with peristaltic mixing, water absorption and absorption of fermentation products," Appl. Microbiol Biatechnol. 1999, 53(1):108-114.
Mishra et al., "Investigation of organoleptic characteristics in the development of soft chews of calcium carbonate as mineral supplement," Yakugaku Zasshi 2009, 129(12):1537-1544.
Mistry et al., "Evidence of acceptability of oral paediatric medicines: a review," J. Pharm. Pharmacol. 2017, 69(4):361-376.
Mizuochi et al., "Characterization of urinary bile acids in a pediatric BRIC-1 patient: effect of rifampicin treatment," Clin Chim Acta. 2012, 413(15-16):1301-1304.
Moghadamrad et al., "Cholestasis in a patient with gallstones and a normal gamma-glutamyl transferase," Hepatology, 2013, 57(6):2539-2541.
Molly et al., "Development of a 5-step multi-chamber reactor as a simulation of the human intestinal microbial system," Appl. Microbiol. Biatechnol. 1993, 39:254-258.
Morissette et al., "High-throughput crystallization: polymorphs, salts, co-crystals and solvates of pharmaceutical solids," Advanced Drug Delivery Reviews, 2004, 56:275-300.
Mouzaki and Allard, "Non-alcoholic steatohepatitis: the therapeutic challenge of a global epidemic," Annals of Gastroenterology, 2012, 25: 207-217.
Mowat et al., "Respiratory chain complex III [correction of complex] in deficiency with pruritus: a novel vitamin responsive clinical feature," J. Pediatr., 134(3):352-4, Mar. 1999.
Nagasaka et al., "Depletion of high-density lipoprotein and appearance of triglyceride-rich low-density lipoprotein in a Japanese patient with FIC1 deficiency manifesting benign recurrent intrahepatic cholestasis," J Pediatr Gastroenterol Nutr., 2007, 45(1)96-105.
Nagase et al., "Preparation of Benzothiazepine derivatives with activity of brining about high blood GLP-1 concentration," CAPLUS Database, Jul. 2002, retrieved from STN Database on Mar. 31, 2014, https://stneasy.cas.org/tmp/20140331/443268-0025347726-200/349520738.html, 2 pages.
Narchi et al., "Intrahepatic cholestasis in two omani siblings associated with a novel homozygous ATP8B1 mutation, c.379C>G (p.L127V).," Saudi J Gastroenterol. 2017, 23(5):303-305.
Neuman, et al., "Biomarkers in nonalcoholic fatty liver disease," Can. J. Gastroenterol. Hepatol. 2014, 28(11):607-618.
Ng et al., "Autoimmune haemolytic anaemia with giant cell hepatitis and concurrent bile salt export pump deficiency: Challenges in diagnosis and management," Journal of Pediatric Gastroenterology and Nutrition 2018, 66(2):860, Abstract No. H-P-127. Meeting Info: 51st Annual Meeting European Society for Paediatric Gastroenterology, Hepatology and Nutrition, ESPGHAN 2018. Geneva, Switzerland. May 9, 2018-May 12, 2018.
Noe et al., "Impaired expression and function of the bile salt export pump due to three novel ABCB11 mutations in intrahepatic cholestasis," J Hepatol. 2005, 43(3):536-543.
O'Neill et al., "Comparison of efficacy of plant stanol ester and sterol ester: short-term and longer-term studies," American Journal of Cardiology, 96(1A):29d-36D, Jul. 2005.
Okubo et al., "II, Daihyoteki Shikkan no Shinryo to Genkyo to Shorai Tenbo 6. Nanjisei Benpi," The Journal of the Japanese Society of Internal Medicine Jan. 10, 2013 (Jan 10, 2013), 102(1), pp. 83-89.
Pai et al. Compression and evaluation of extended release matrix pellets prepared by the extrusion/spheronization process into disintegrating tablets. Brazilian Journal of Pharmaceutical Sciences, vol. 48, n. 1, janinnar., 2012 (Year: 2012).
Painter et al., "Sequence variation in the ATP8B1 gene and intrahepatic cholestasis of pregnancy," Eur J Hum Genet. 2005, 13(4):435-439.
Park et al., "Clinical and ABCB11 profiles in Korean infants with progressive familial intrahepatic cholestasis," World J Gastroenterol., 2016, 22(20):4901-4907.
Parker et al., "Molecular mechanisms underlying bile acid-stimulated glucagon-like peptide-1 secretion," British J. Pharmacology, 2012, 165:414-423.
Patani et al., "Bioisosterism: A Rational Approach in Drug Design," Chem Rev, 1996, 96:3147-3176.
Pattni and Walters, "Recent advances in the understanding of bile acid malabsorption," Br. Med. Bull. 2009, vol. 92, p. 79-93.
Pauli-Magnus et al., "Enterohepatic transport of bile salts and genetics of cholestasis," Journal of Hepatology, 2005, 43(2):342-357.
Pauli-Magnus et al., "Impaired expression and function of the bile salt export pump due to three novel ABCB11 mutations in intrahepatic cholestasis," Hepatology 2003, vol. 38, No. 4 Suppl. 1, pp. 518A. print. Meeting Info.: 54th Annual Meeting of the American Association for the Study of Liver Diseases. Boston, MA, USA. Oct. 24-28, 2003. American Association for the Study of Liver Diseases.

(56) References Cited

OTHER PUBLICATIONS

Peng et al., "[Relationship between phenotype and genotype of ABCB11 deficiency in siblings and literature review].," Zhonghua er ke za zhi (Chinese journal of pediatrics) 2018, 56(6):440-444.
Perez et al., "Bile-acid-induced cell injury and protection," World J Gastroenterol, Apr. 2009, 15(14)1677-1689.
Perumpail et al., "Clinical epidemiology and disease burden of nonalcoholic fatty liver disease," World Journal of Gastroenterology, Dec. 2017, 23(47): 8263-8276.
Plump et al., "Severe hypercholesterolemia and atherosclerosis in apolipoprotein E-deficient mice created by homologous recombination in ES cells", Cell (71):343-353, 1992.
Podesta et al., "Treatment of pruritus of primary biliary cirrhosis with rifampin," Dig. Dis. Sci, 1991, 36(2):216-220.
Possemiers et al., "PCR-DGGE-based quantification of stability of the microbial community in a simulator of the human intestinal microbial ecosystem," FEMS Microbiol. Ecol. 2004, vol. 49, p. 495-507.
Poupon et al., "Chronic Cholestatic Disease," J. Hepatology, 2000, 32(1):12-140.
Qiu et al., "Defects in myosin VB are associated with a spectrum of previously undiagnosed low γ-glutamyltransferase cholestasis," Hepatology 2017, 65(5)1655-1669.
Qiu et al., "Disruption of BSEP function in HepaRG cells alters bile acid disposition and is a susceptive factor to drug-induced cholestatic injury," Mol. Pharmaceutics, 13:4,, 2016 (Abstract only).
Reeder et al., "Quantitative assessment of liver fat with magnetic resonance imaging and spectroscopy," J Magn Reson Imaging. 2011, 34(4):729-749.
Renga et al., "Role of FXR in regulating bile acid homeostasis and relevance for human diseases," Curr. Drug. Targets Immune Endocr. Metabol. Disord., 5(3):289-303, Sep. 2005.
Report EC20082069.02.01 dated Feb. 2009, filed with appellant's letter of Apr. 26, 2011.
Report filed at oral proceedings before opposition division, GMS-CFEP-2007-20, "Filtration and Drying Study on Amorphous and Form IV Atorvastatin Calcium," 2007.
Rolo et al., "Bile acids affect liver mitochondrial bioenergetics: Possible relevance for cholestasis therapy," Toxocological Sciences, 57: 177-185, 2000.
Rumbo et al., Transplantation 2018, vol. 102, No. 7, Supp. Supplement 1, pp. S848. Abstract No. P.752. Meeting Info: 27th International Congress of The Transplantation Society, TTS 2018, Madrid, Spain, Jun. 30, 2018-Jul. 5, 2018.
Sanyal et al. The etiology of hepatocellular carcinonna and consequences of treatment. The Oncologist, 2010, 15 Suppl 4, 14-22.
Satapathy and Sanyal, "Epidemiology and Natural History of Nonalcoholic Fatty Liver Disease," Seminars in Liver Disease, Aug. 2015, 35(3): 221-235.
Sattler et al., "Functional analysis of previously uncharacterised disease-causing mutations of the bile salt export pump," Journal of Hepatology 2017, 66(1):5177. Meeting Info.: International Liver Congress/ 52nd Annual Meeting of the European-Association-for-the-Studyof- the-Liver. Amsterdam, Netherlands. Apr. 19-23, 2017, European Assoc Study Liver.
Scheimann et al., "Prevalence of Abcb 11 mutations among children with cholelithiasis," Gastroenterology 2007, 132(4)Suppl. 2:A452, Meeting Info.: Digestive Disease Week Meeting/108th Annual Meeting of the American-GastroenterologicalAssociation. Washington, DC, USA. May 19-24, 2007. Amer Gastroenterol Assoc; Amer Assoc Study Liver Dis; Amer Soc Gastrointestinal Endoscopy; Soc Surg Alimentary Tract.
Scheuer, "Primary Biliary Cirrhosis," Proc. R. Soc. Med., Dec. 1967, 60:1257-1260.
Schiller, "Review article: the therapy of constipation", Alimentary Pharmacology and Therapeutics 15(6):749-763, 2001.
Schumpelick et al., "[Ulcerative colitis—late functional results of ileoanal pouch anastomosis]," Chirung, 69(10):1013-19, Oct. 1998.
Sciveres. "Relapsing features of bile salt export pump (BSEP) deficiency in a patient successfully transplanted for progressive familial intrahepatic cholestasis type 2 (PFIC2).," Digestive and Liver Disease 2010, 42(5):5329. Abstract No. CO18, Meeting Info: 17th National Congress SIGENP, Pescara, Italy. Oct. 7, 2010-Oct. 9, 2010.
Shah et al., "Progressive Familial Intrahepatic Cholestasis Type 2 in an Indian Child," J Pediatr Genet. 2017, 6(2):126-127.
Shah et al., "Role of Caco-2 Cell Monolayers in Prediction of Intestinal Drug Absortption," Biotechnol. Prog., 2006, 22:186-198.
Shang et al., "Colesevelam improves insulin resistance in a diet-induced obesity (F-DIO) rat model by increasing the release of GLP-1," Am J. Physiol Gastrointest Liver Physiol, 2010, 298:G419-G424.
Shaprio et al., "DHPLC screening for mutations in progressive familial intrahepatic cholestasis patients," J Hum Genet. 2010, 55(5):308-313.
Sharma et al., "Spectrum of genomic variations in Indian patients with progressive familial intrahepatic cholestasis," BMC Gastroenterol, 2018, 18(1):107.
Sharma et al., "Spectrum of sequence variations in Indian patients with progressive familial intrahepatic cholestasis show several novel polymorphisms," Indian Journal of Gastroenterology 2017, 36(1):A99. Abstract No. M-20. Meeting Info: 58th Annual Conference of the Indian Society of Gastroenterology, ISGCON 2017, Bhubaneswar, India. Dec. 14, 2017-Dec. 17, 2017.
Sherrif et al., "Hepatotoxicity from anabolic androgenic steroids marketed as dietary supplements: contribution from ATP8B1/ABCB11 mutations?," Liver international: official journal of the International Association for the Study of the Liver, 2013, 33(8):1266-1270.
Shimizu et al., "Living-related liver transplantation for siblings with progressive familial intrahepatic cholestasis 2, with novel genetic findings," Am J Transplant. 2011, 11(2):394-398.
Simons, "The fate of the orally administered bile acid sequestrant, polidexide, in humans," Clin. Exp. Pharmacol. Physiol., 3(1):99-101, Jan.-Feb. 1976.
Singhal et al., "Drag polymorphism and dosage form design: a practical perspective," Adv Drug Deliv Rev, Feb. 23, 2004, 56(3):335-347.
Sinha and Kumria, "Microbially triggered drag delivery to the colon," Eur. J. Pharm. Sci. 2003, vol. 18, p. 3-18.
Sirtori, "Mechanisms of lipid-lowering agents," Cardiology, 78(3):226-35, 1991.
Sohn et al., "Benign Recurrent Intrahepatic Cholestasis Type 2 in Siblings with Novel ABCB11 Mutations," Pediatr Gastroenterol Hepatol Nutr. 2019, 22(2):201-206.
Sorrentino et al., "A Clinical-Morphological Study on Cholestatic Presentation of Nonalcoholic Fatty Liver Disease," Digestive Disease and Sciences, Jun. 2005, 50(6):1130-1135.
Sprong et al., "Dietary Calcium Phosphate Promotes Listeria monosytogenes colonization and translocation in rats red diets containing corn oil but not milk fat1", J. Nutrition (US) 132(6):1269-1274, 2002.
Squires et al., "Clinical Variability After Partial External Biliary Diversion in Familial Intrahepatic Cholestasis 1 Deficiency," J Pediatr Gastroenterol Nutr. 2017, 64(3):425-430.
Staels and Kuipers, "Bile Acid Sequestrants and the Treatment of Type 2 Diabetes Mellitus," Drugs, 2007, 67(10):1383-1392.
Staels and Kuipers, "Bile acid sequestrants and the treatment of type 2 diabetes mellitus," Drugs, 67(10):1383-92, 2007.
Stein, "Managing Dyslipidemia in the High-Risk Patient," Am J. Cardiol., 2002, 89:50-57.
Stindt et al., "A novel mutation within a transmembrane helix of the bile salt export pump (BSEP, ABCB11) with delayed development of cirrhosis," Liver Int. 2013, 33(10):1527-1735.
Stolz et al., "Severe and protracted cholestasis in 44 young men taking bodybuilding supplements: assessment of genetic, clinical and chemical risk factors," Aliment Pharmacol Ther. 2019, 49(9):1195-1204.
Stone et al., "Biochemical characterization of P4-ATPase mutations identified in patients with progressive familial intrahepatic cholestasis," J Biol Chem. 2012, 287(49)41139-51.

(56) References Cited

OTHER PUBLICATIONS

Strautnieks et al., "Severe bile salt export pump deficiency: 82 different ABCB11 mutations in 109 families," Gastroenterology, 2008, 134(4):1203-1214.
Sun et al., "Bile acids promote diethylnitrosamine-induced hepatocellular carcinoma via increased inflammatory signaling," American Journal of Physiology—Gastrointestinal and Liver Physiology, May 5, 2016, 311(1):G91-104.
Suzuki and Takada, "Mechanisms of regulation of bile acid transport in the small intestine," Falk Symposium, 165:76-81, 2009.
Swedish Office Action for Swedish Appln. No. 1850915-8, dated Feb. 15, 2019, 6 pages.
Swedish Search Report for Swedish Appln. No. 1850915-8, dated Feb. 15, 2019, 2 pages.
Takahashi et al., "Gradual improvement of liver function after administration of ursodeoxycholic acid in an infant with a novel ABCB11 gene mutation with phenotypic continuum between BRIC2 and PFIC2," Eur J Gastroenterol Hepatol. 2007, 19(11):942-6.
Tanaka et al., "Genetic and Familial considerations of Primary Biliary Cirrhosis," Am. J. Gastroenterology, 2001, 96(1): 8-15.
Tibesar et al., "Two Cases of Progressive Familial Intrahepatic Cholestasis Type 2 Presenting with Severe Coagulopathy without Jaundice," Case Rep Pediatr. 2014, 2014:185923.
Togawa et al., "Diversity of ATP8B1 mutations in japanese patients with intrahepatic cholestasis associated with low gamma-glutamyl transpeptidase level," Journal of Pediatric Gastroenterology and Nutrition 2018, 67(1):S363, Abstract No. 615.
Tollefson et al., "A novel class of apical sodium co-dependent bile acid transporter inhibitors: the 1,2-Benzothiazepines", Bioorganic and Medicinal Chemistry Letters 12:3727-3730, 2003.
Treepongkaruna et al., "Novel ABCB11 mutations in a Thai infant with progressive familial intrahepatic cholestasis," World J Gastroenterol. 2009, 15(34):4339-4342.
Tremont et al., "Discovery of Potent, Nonsystemic Apical Sodium-Codependent Bile Acid Transporter Inhibitors (Part 1)," J. Med. Chem, 2005, 48:5837-5852.
Tyle, "Effect of size, shape and hardness of particles in suspension on oral texture and palatability," Acta Psychologica 1993, 84(1):111-118.
Uegaki et al., "Successful treatment with colestimide for a bout of cholestasis in a Japanese patient with benign recurrent intrahepatic cholestasis caused by ATP8B1 mutation," Intern Med. 2008, 47(7):599-602.
Van der Woerd et al., "Analysis of aberrant pre-messenger RNA splicing resulting from mutations in ATP8B1 and efficient in vitro rescue by adapted U1 small nuclear RNA," Hepatology 2015, 61(4):1382-1391.
Van der Woerd et al., "Mutational analysis of ATP8B1 in patients with chronic pancreatitis," PLoS One. 2013, 8(11):e80553.
Van Heek et al., "In vivo metabolism-based discovery of a potent cholesterol absorptions inhibitor, sch58235, in the rat and rhesus monkey through the identification of the active metabolites of sch48461," J. Pharmacol. Exp. Med, 1997, 283(1):157-163.
Van Mil et al., "Benign recurrent intrahepatic cholestasis type 2 is caused by mutations in ABCB11," Gastroenterology. 2004, 127(2):379-384.
Van Tilberg et al., "Na+-dependent bile acid transport in the ileum: the balance between diarrhea and constipation", Gastroenterology 98(1):25-32, 1989.
Varma et al., "Retargeting of bile salt export pump and favorable outcome in children with progressive familial intrahepatic cholestasis type 2," Hepatology 2015, 62(1):198-206.
Vaz et al., "Sodium taurocholate cotransporting polypeptide (SLC10A1) deficiency: conjugated hypercholanemia without a clear clinical phenotype," Hepatology, 2015, 61(1):260-267.
Vertommen and Kinget, "The influence of five selected processing and formulation variables on the particle size, particle size distribution, and friability of pellets produced in a rotary processor," Drug Dev. Ind. Pharm. 1997, vol. 23, p. 39-46.
Vippagunta et al., "Crystalline solids", Advanced Drug Delivery Reviews 48:3-26, 2001.
Vitale et al., "Cryptogenic cholestasis in young and adults: ATP8B1, ABCB11, ABCB4, and TJP2 gene variants analysis by high-throughput sequencing," J Gastroenterol. 2018, 53(8):945-958.
Waisbourd-Zinman et al., "A Rare BSEP Mutation Associated with a Mild Form of Progressive Familial Intrahepatic Cholestasis Type 2," Ann Hepatol. 2017, 16(3):465-468.
Walkowiak-Tomczak, "Characteristics of plums as a raw material with valuable nutritive and dietary properties—a review," Pol. J. Food Nutr. Sci., 58(4):401-405, 2008.
Walsh et al., "Patient acceptability, safety and access: A balancing act for selecting age-appropriate oral dosage forms for paediatric and geriatric populations," Int. J. Pharm. 2017, 536(2):547-562.
Wang et al., "Bile acid receptors and liver cancer," Curr. Pathobiol Rep, Mar. 2013, 1(1):29-35.
Wang et al., "Increased hepatocellular carcinoma risk in chronic hepatitis B patients with persistently elevated serum total bile acid: a retrospective cohort study," Scientific reports, Dec. 1, 2016, 6:38180, 9 pages.
Wang et al., "Splicing analysis of rare/novel synonymous or intronic variants identified in ABCB11 heterozygotes presenting as progressive intrahepatic cholestasis with low γ-glutamyltransferase," Hepatol Res. 2018, 48(7):574-584.
Wang et al., "The Features of GGT in Patients with ATP8B1 or ABCB11 Deficiency Improve the Diagnostic Efficiency," PLoS One. 2016; 11(4):e0153114.
Watts and Illum, "Colonic Drug Delivery," Drug Development and Industrial Pharmacy, 1997, 23(9):893-913.
Welberg et al., "Calcium and the prevention of colon cancer", Scandinavian J. Gasteroenterology Suppl. 188:52-59, 1991.
Whitington et al., "Partial external diversion of bile for the treatment of intractable pruritus associated with intrahepatic cholestasis," Gastroenterology, 95: 1, 130-136, 1988 (Abstract only).
Williams et al., Foye's Principles of Medicinal Chemistry, 5th Edition, 2002, 59-63.
Wolff, "Burger's Medicinal Chemistry, 5ed, Part I", John Wiley & Sons, 1995, pp. 975-977.
Wong et al., "Utility of oligonucleotide array-based comparative genomic hybridization for detection of target gene deletions," Clin Chem. 2008, 54(7)1141-1148.
Woolbright et al., "Novel insight into mechanisms of cholestatic liver injury," World Journal of Gastroenterology, 18: 36, 4985-4993, 2012.
Wu et al., "Discovery of a highly potent, nonabsorbable apical sodium-dependent bile acid transporter inhibitor (GSK2330672) for treatment of type 2 diabetes," J. Med. Chem., 2013, 53(12):5094-5117.
Xie et al., "Dysregulated hepatic bile acids collaboratively promote liver carcinogenesis," Int J Cancer, Oct. 15, 2016, 139(8):1764-1775.
Yang et al., "Partial external biliary diversion in children with progressive familial intrahepatic cholestasis and alagille disease," Journal of Pediatric Gastroenterology and Nutrition, 49: 216-221, 2009.
Yerushalmi et al., "Bile acid-induced rat hepatocyte apoptosis is inhibited by antioxidants and blockers of the mitochondrial," Hepatology, 33: 3, 616-626, 2001.
Zarenezhad et al., "Investigation of Common Variations of ABCB4, ATP8B1 and ABCB11 Genes in Patients with Progressive Familial Intrahepatic Cholestasis," Hepatitis Monthly: 2017, 17(2):e43500.
Zhang et al., "Effect of bile duct ligation on bile acid composition in mouse serum and liver," Liver int, 32: 1, 58-69, 2012.
Zhang et al., Abcb11 deficiency induces cholestasis coupled to impaired B-Fatty acid oxidation in mice, Journal of biological chemistry, 287: 29, 24784-2479, 2012.

* cited by examiner

IN VITRO METHOD FOR DETERMINING THE ADSORBING CAPACITY OF AN INSOLUBLE ADSORBANT

CROSS-REFERENCE TO RELATED APPLICATIONS

This application claims priority to U.S. provisional application No. 62/716,523, filed Aug. 9, 2018, the disclosure of which is incorporated by reference herein in its entirety.

TECHNICAL FIELD

The invention relates to an in vitro method for determining the adsorbing capacity of an adsorbent having limited solubility, such as a bile acid sequestrant, under conditions simulating the mammalian gastrointestinal tract. The method is particularly useful for studying the release profiles of controlled release formulations comprising adsorbents having limited solubility.

BACKGROUND

In vitro simulation technologies offer an alternative or complementary approach for human or animal studies. In complete in vitro gastrointestinal models, the kinetics of the gut are simulated by controlling the concentrations of gastric, small intestinal and pancreatic enzymes, bile, pH, temperature, feed composition, transit time in the gastrointestinal tract and the anaerobic environment with physiological relevance. Such models have e.g. been reported by Allison et al. (*Appl. Environ. Microbiol.* 1989, vol. 55, p. 672-678), Molly et al. (Appl. Microbiol. Biotechnol. 1993, vol. 39, p. 254-258) and Minekus et al. (Appl. Microbiol Biotechnol. 1999, vol. 53, p. 108-114).

The intestinal tract is a very complex and diverse ecosystem, comprising up to $10^{14}$ cells of 300-500 different microbial species (Hill, M. J. (1995) Role of Gut Bacteria in Human Toxicology and Pharmacology. Taylor & Francis, London. 286 pp). The intestinal microbial community plays a significant role in processes of food digestion, bioconversion of endogenous or exogenous compounds, immunomodulation, and prevention from infection by intestinal pathogens (Gibson and Roberfroid, *J. Nutr.* 1995, vol. 125 (6), p. 1401-1412; Fuller, *J. Appl. Bacteriol.* 1989, vol. 66(5), p. 365-378). A good understanding of the fate of a pharmaceutical product in the gastrointestinal tract is therefore very valuable. In vitro gastrointestinal models may in that respect serve as helpful tools in the pre-clinical development of a pharmaceutical product, as they may provide important information on the product's solubility, release, stability and bioavailability under conditions simulating the stomach, the small intestine and the colon.

The low solubility of certain compounds, such as bile acid sequestrants, in aqueous environment prevents measuring the concentrations of these compounds. This restricts the possibilities of studying such compounds in an in vitro gastrointestinal model.

Bile acid sequestrants, such as colesevelam, cholestyramine and colestipol, are polymeric resins that are used to bind bile acids in the lower gastrointestinal tract. In the colon, the sequestrant and the bile acid form an insoluble complex, which is then excreted in the faeces. The sequestrant thereby prevents the normal reabsorption of bile acids from the gut. However, bile acid sequestrants are also known to interact with other drugs administered concomitantly and to induce risks for malabsorption of fat and fat-soluble vitamins. In order to minimize the risk for undesired interactions with other compounds in the gastrointestinal tract, it is preferred that the release of sequestrant should be as little as possible before it reaches the lower part of the small intestine. Therefore, oral formulations of sequestrants are preferably administered to a patient as a targeted release formulation that specifically releases the sequestrants in the proximal part of the colon.

Because bile acid sequestrants are not soluble in aqueous environment, they are not "released" from formulations comprising them (such as a targeted release formulations) in that they dissolve and diffuse into the intestine. It is therefore difficult to determine the release profile (i.e., a profile of the availability to the intestinal content) of a bile acid sequestrant when administered as a controlled release formulation, such as a targeted release formulation.

In view of the above, there is a need for improved methods that make it possible to study the behavior of insoluble compounds in in vitro gastrointestinal models. Such methods would in particular be useful for studying release profiles of targeted release formulations comprising insoluble compounds.

DETAILED DESCRIPTION OF THE INVENTION

The present invention relates to an in vitro method for determining the availability to the intestinal content of an adsorbent having limited solubility, under conditions simulating the gastrointestinal tract, i.e. at pH values, microbial conditions and transit times that are representative of digestion in the stomach, the small intestine and the colon. The method involves the addition of a marker compound, which is a compound that is adsorbed by the adsorbent. Measuring the decreasing concentration of the free marker compound in the simulated gastrointestinal tract provides an adsorption profile of the adsorbent in the gastrointestinal tract.

Thus, in a first embodiment, the invention relates to an in vitro method for determining the adsorbing capacity of an adsorbent having limited solubility, under conditions simulating the mammalian gastrointestinal tract, wherein the method comprises the steps of:
 a) providing a liquid medium representative of at least one region of the gastrointestinal tract;
 b) adding to said liquid medium defined amounts of an adsorbent and a marker compound; and c) incubating the mixture obtained in step b) and measuring the amount of free marker compound in said mixture.

As used herein, the term "adsorbent" refers to a compound that is able to bind and complex with a compound in the gastrointestinal tract. The adsorbents used in the in vitro method described herein have limited solubility. Examples of adsorbents with limited solubility include, but are not limited to, polymeric resins such as bile acid sequestrants; activated carbon; hydrated aluminium silicate (kaolin); and insoluble dietary fiber.

The compound that is adsorbed by the adsorbent may be a compound that causes undesired effects in the gastrointestinal tract, such as a poison, a lipoprotein, a bile acid or a drug. As the adsorbent forms an insoluble complex with the undesired compound, the latter may be effectively removed from the gastrointestinal tract and its activity disrupted. The undesired compound may be used as a marker compound in the in vitro method described herein.

As used herein, the term "limited solubility" means that the adsorbent is insoluble, or has only low solubility in aqueous conditions, such as less than 10% solubility, such as less than 5% solubility, e.g. less than 4%, less than 3%, less than 2% or less than 1% solubility.

Measuring the amount of free marker compound includes the steps of collecting a sample from the mixture and analyzing the sample. By analyzing samples collected after different incubation times, the decrease of free marker compound can be followed over time.

The mammalian gastrointestinal tract may be representative of a human or of an animal such as dog, cat, pig, horse, cow or sheep. In a preferred embodiment, the gastrointestinal tract is representative of a human.

The in vitro method is performed at normal body temperature for the mammal. The normal body temperature for a human is about 37° C.

The term "conditions simulating the gastrointestinal tract" refers to conditions that are representative of digestion in the stomach, the small intestine and the colon. The simulation may involve one or more parameters that are representative of digestion in the stomach, the small intestine and the colon, including, but not limited to, the pH; the transit times; the presence and concentration of specific enzymes; the presence and concentration of specific salts; the presence and concentration of specific acids; and the presence and composition of intestinal microbiota.

In one embodiment, the simulation conditions simulating the gastrointestinal tract are conditions simulating the stomach, the small intestine or the colon. In a preferred embodiment, the conditions simulating the mammalian gastrointestinal tract are conditions simulating the stomach and the small intestine. In another preferred embodiment, the conditions simulating the mammalian gastrointestinal tract are conditions simulating the small intestine and the colon. In a most preferred embodiment, the conditions simulating the mammalian gastrointestinal tract are conditions simulating the stomach, the small intestine and the colon. When the conditions simulating the mammalian gastrointestinal tract are conditions simulating two or more regions of the gastrointestinal tract, the method involves the additional step(s) of converting the liquid medium representative for a first region of the gastrointestinal tract to a liquid medium representative for the next region of the gastrointestinal tract, as outlined herein below.

When the method simulates the conditions for at least the stomach and the small intestine, the marker compound may be added either to the liquid medium representative of the stomach or to the liquid medium representative of the small intestine, i.e. after conversion of the liquid medium representative of the stomach to a liquid medium representative of the small intestine. Addition of the marker compound to the liquid medium representative of the small intestine may be preferable when the marker compound is not stable under the conditions representative of the stomach, or when the marker compound is naturally occurring in the small intestine but not in the stomach, such as a bile salt.

In one embodiment, the conditions simulating the gastrointestinal tract are conditions simulating a healthy individual. In another embodiment, the conditions simulating the gastrointestinal tract are conditions simulating an individual suffering from a disease, such as a gastrointestinal disease. The conditions may then comprise e.g. the pH, transit times, enzymes, salts, acids and microbiota that are representative for the gastrointestinal tract of an individual suffering from said disease.

The liquid medium representative of at least one region of the gastrointestinal tract is an aqueous mixture comprising salts, acids, enzymes and/or microbiota that are typically present in the stomach, the small intestine or the colon.

The liquid medium representative of the stomach resembles gastric juice. It comprises hydrochloric acid, and may further comprise enzymes, such as pepsin, and salts, such as NaCl or KCl. It may also comprise mucin. The stomach liquid medium has a pH between about 1.5 and about 3, more preferably between about 1.5 and about 2.5, and more preferably between about 1.5 and about 2. In a most preferred embodiment, the pH of the stomach liquid medium is about 1.8.

Depending on the amount of food present in the stomach, the transit time in the human stomach normally ranges from about 30 minutes up to about 4 hours. The mixture of stomach liquid medium, adsorbent and marker compound may therefore be incubated for at least about 30 minutes, such as at least about 1 hour. The mixture may be incubated for up to about 2 hours, or up to about 3 hours, or up to about 4 hours.

The liquid medium representative of the small intestine resembles pancreatic juice. It has a pH between about 6 and about 7.5, more preferably between about 6.5 and about 7. In a most preferred embodiment, the pH of the small intestine liquid medium is about 6.8. The small intestine liquid medium may also comprise enzymes, such as pancreatin, and furthermore bile acids or salts.

The transit time in the human small intestine normally ranges from about 1.5 to about 4 hours. The mixture of small intestine liquid medium, adsorbent and marker compound may therefore be incubated for at least about 1.5 hours, such as at least about 2 hours. The mixture may be incubated for up to about 3 hours, or up to about 4 hours.

The liquid medium representative of the colon has a pH between about 5 and about 7, more preferably between about 5.5 and about 6.5. In a most preferred embodiment, the pH of the colon liquid medium is about 6.0. The colon liquid medium may further comprise a microbial community that is representative of the colon (also referred to as matrix).

The microbial community representative of the colon may comprise intestinal microorganisms, such as bacteria, for example from the genera *Lactobacillus, Bacteroides, Clostridium, Faecalibacterium, Eubacterium, Ruminococcus, Peptococcus, Peptostreptococcus, Staphylococcus, Enterococcus, Bifidobacterium* and *Escherichia*; and fungi, for example from the genera *Candida, Saccharomyces, Aspergillus,* and *Penicillium*. The colon liquid medium preferably comprises a stable microbial community, i.e.

microsystem wherein the microbial population does not change over time. A method for obtaining a stable microbial community of the human intestine is described by Possemiers et al. (*FEMS Microbiol. Ecol.* 2004, vol. 49, p. 495-507) and references therein.

The transit time in the human colon (comprising the ascending, transverse and descending colon) normally ranges from about 26 to about 58 hours. The mixture of colon liquid medium, adsorbent and marker compound may therefore be incubated for at least about 12 hours, such as at least about 18 hours, such as at least about 24 hours. The mixture may be incubated for up to about 36 hours, or up about 48 hours, or up to about 60 hours, or up to about 72 hours.

The colon comprises three regions having their own microbial community, namely the ascending, transverse and descending colon. In one embodiment, the simulation of the gastrointestinal tract comprises the stomach, the small intestine and the ascending colon. In another embodiment, the simulation of the gastrointestinal tract comprises the stomach, the small intestine, the ascending and the transverse colon. In yet another embodiment, the simulation of the gastrointestinal tract comprises the stomach, the small intestine, and the ascending, the transverse colon and the descending colon.

Thus, in another embodiment, the invention relates to an in vitro method for determining the adsorbing capacity of an adsorbent having limited solubility, under conditions simulating the mammalian gastrointestinal tract, wherein the method comprises the steps of:
  a) providing a liquid medium representative of the stomach;
  b) adding to said liquid medium defined amounts of an adsorbent and a marker compound;
  c) incubating the mixture obtained in step b) and measuring the amount of free marker compound in said mixture;
  d) converting the mixture of step c) to a medium representative of the small intestine;
  e) incubating the mixture obtained in step d) and measuring the amount of free marker compound in said mixture;
  f) converting the mixture of step e) to a medium representative of the ascending colon; and
  g) incubating the mixture obtained in step f) and measuring the amount of free marker compound in said mixture.

In step d), the medium representative of the stomach is converted to a medium representative of the small intestine addition. This conversion may be achieved by the addition of enzymes representative of the small intestine, such as pancreatin, and by adjustment of the pH. Additional salts, acids, enzymes and microbiota typically present in the small intestine may also be added. In a preferred embodiment, bile acids or salts are added to the medium representative of the small intestine.

In step f), the medium representative of the small intestine is converted to a medium representative of the ascending colon. This conversion may be achieved by the addition of a microbial community representative of the ascending colon and by adjustment of the pH. Additional salts, acids, enzymes and microbiota typically present in the colon may also be added.

In yet another embodiment, the invention relates to an in vitro method for determining the adsorbing capacity of an adsorbent having limited solubility, under conditions simulating the mammalian gastrointestinal tract, wherein the method comprises the steps of:
  a) providing a liquid medium representative of the stomach;
  b) adding to said liquid medium a defined amount of an adsorbent;
  c) incubating the mixture obtained in step b);
  d) converting the mixture of step c) to a medium representative of the small intestine;
  e) adding a defined amount of a marker compound to the mixture of step d);
  f) incubating the mixture obtained in step e) and measuring the amount of free marker compound in said mixture;
  g) converting the mixture of step f) to a medium representative of the ascending colon; and
  h) incubating the mixture obtained in step g) and measuring the amount of free marker compound in said mixture.

The marker compound may not be sufficiently stable to completely survive the conditions simulating the gastrointestinal tract, and may be partially degraded. In particular, the marker compound may be slowly degraded (or metabolized) by the presence of e.g. salts, acids, enzymes and microbiota in the liquid media. The measured amounts of free marker compound may then not be fully accurate. In such case, a control experiment to which no adsorbent is added may be performed in order to determine the amount of degradation of the marker compound. The measured amounts of the free marker compound in a real experiment may then be corrected for the degradation observed in the control experiment.

The adsorbent may be added in pure form or as a pharmaceutical formulation comprising the adsorbent. In particular, the adsorbent may be formulated as a controlled release formulation, such as a delayed release or targeted release formulation. The in vitro method then provides a "release profile" of the adsorbent formulation in the gastrointestinal tract. The method may therefore be a useful tool in the development of a controlled release formulation of an adsorbent. It should be noted that as the adsorbent has limited solubility, or is not soluble at all, it may not actually be released from a formulation comprising it in that it dissolves and diffuses into the intestine. Therefore, as used herein, the term "release" of the adsorbent refers to the availability of the adsorbent to the intestinal content in order to bind components therein.

In a preferred embodiment, the adsorbent is a bile acid sequestrant. Examples of bile acid sequestrants include cholestyramine, colestipol, colesevelam, colextran and colestilan. In a more preferred embodiment, the bile acid sequestrant is cholestyramine.

When the adsorbent is a bile acid sequestrant, the marker compound preferably is a bile acid such as cholic acid, chenodeoxycholic acid or deoxycholic acid, or a derivative thereof, or a bile acid salt thereof. A mixture comprising two or more different bile acids or bile acid salts may also be used.

Therefore, in another embodiment, the invention relates to an in vitro method for determining the sequestering capacity of a bile acid sequestrant under conditions simulating the mammalian gastrointestinal tract, wherein the method comprises the steps of:
  a) providing a liquid medium representative of at least one region of the gastrointestinal tract;
  b) adding defined amounts of a bile acid sequestrant and of one or more bile acids;

c) incubating the mixture and measuring the amount of free bile acid in the mixture.

The method described herein is particularly useful for determining the sequestering capacity of a bile acid sequestrant that is formulated for controlled release, such as a targeted release formulation. Such formulations are e.g. disclosed in EP 1273307, WO 2017/138877, WO 2017/138878, WO 2019/032026, WO 2019/032027, U.S. Ser. No. 16/100,048 and U.S. Ser. No. 16/100,055, all of which are hereby incorporated by reference in their entireties.

Because of their very low solubility, bile acid sequestrants are not "released" from formulations comprising them in that they dissolve and diffuse into the intestine. Instead, they probably stay within the gradually degrading structure of the formulation. Therefore, as used herein, the term "release" of the sequestrant refers to the availability of the sequestrant to the intestinal content in order to bind components (e.g. bile acids) therein.

Preferably, the invention relates to an in vitro method for determining the sequestering capacity of a bile acid sequestrant under conditions simulating the mammalian gastrointestinal tract, wherein the method comprises the steps of:
a) providing a liquid medium representative of the stomach;
b) adding a defined amount of a bile acid sequestrant;
c) incubating the mixture obtained in step b);
d) converting the mixture of step c) to a medium representative of the small intestine;
e) adding a defined amount of one or more bile acids to the mixture obtained in step d);
f) incubating the mixture obtained in step e) and measuring the amount of free bile acid in the mixture;
g) converting the mixture of step f) to a medium representative of the colon; and
h) incubating the mixture obtained in step g) and measuring the amount of free bile acid in the mixture.

The one or more bile acids that are added in step b) may be cholic acid (CA), chenodeoxycholic acid (CDCA) or deoxycholic acid (DCA), or a derivative thereof, or a mixture comprising two or more different bile acids. The bile acid(s) may also be added as the corresponding bile salt(s). In a preferred embodiment, a mixture comprising CA, CDCA and DCA is added. Preferably, the ratio between CA, CDCA and DCA is 40:40:20 (w/w). Such a mixture is highly similar to the bile salt pool in humans and under physiological conditions (Carulli et al., *Aliment. Pharmacol. Ther.* 2000, vol. 14, issue supplement s2, p. 14-18).

The analysis of the samples may be performed by chromatography, in particular liquid chromatography such as high performance liquid chromatography, e.g. reversed phase HPLC using an octadecyl carbon chain (C18)-bonded silica column. A calibration curve for the chromatography system may be prepared for calculating the concentrations of the non-sequestered compounds, such as bile salts, in the samples.

In some embodiments, the sequestering capacities of a formulation comprising a bile acid sequestrant is determined using the Simulator of the Human Intestinal Microbial Ecosystem (SHIME®) as developed by ProDigest (Ghent, Belgium). As described in more detail in the experimental section, this model enables the in vitro evaluation of the bile acid binding capacity of a formulation comprising a bile acid sequestrant under physiological conditions representative of a fasted stomach, small intestine and proximal colon. Bile acids such as cholic acid (CA), chenodeoxycholic acid (CDCA) and deoxycholic acid (DCA), or a mixture of two or more of these bile salts, may be used in such studies. For example, a 40:40:20 (w/w) mixture of CA, CDCA and DCA can be used as a representative mixture of human bile salts. In some embodiments, experiments on bile acid sequestrant formulations are run in parallel with a control experiment to which no bile acid sequestrant is added, in order to monitor the degradation of the bile salts under the conditions used in the assay. For each such experiment, samples may be taken at selected time intervals and the concentrations of the bile acids in the samples may be determined, e.g. by means of HPLC. From these data, the percentage of remaining bile acids in each studied sample may be calculated as the ratio of the value of the studied sample to the value of the control sample at the corresponding incubation time:

$$\% \text{ remaining bile acid} = \frac{\text{concentration of } BA \text{ in sample}}{\text{concentration of } BA \text{ in control sample}} \times 100$$

A plot of the percentage of remaining bile acids against time will show the decrease of bile acids, i.e. the sequestration of bile acids by the bile acid sequestrant, during small intestinal and colonic incubation.

As used herein, the term "about" refers to a value or parameter herein that includes (and describes) embodiments that are directed to that value or parameter per se. For example, description referring to "about 20" includes description of "20." Numeric ranges are inclusive of the numbers defining the range. Generally speaking, the term "about" refers to the indicated value of the variable and to all values of the variable that are within the experimental error of the indicated value (e.g., within the 95% confidence interval for the mean) or within 10 percent of the indicated value, whichever is greater.

EXAMPLES

Methods and Materials

SHIME® experiments were performed in the Simulator of the Human Intestinal Microbial Ecosystem as developed by ProDigest (Ghent, Belgium).

Oxgall, a dehydrated fresh bile extract from bovine origin was obtained from BD Difco™ (Catalog Number 212820). Cholic acid (CA), chenodeoxycholic acid (CDCA) and deoxycholic acid (DCA) were obtained from Sigma-Aldrich.

Example 1

Determination of the Sequestering Capacity of Cholestyramine Formulations Under Conditions Representative of the Stomach and the Small Intestine The sequestering capacities of three different colon release formulations (A-C) were determined in an assay simulating the conditions of the stomach and the small intestine. The sequestration was determined by measuring the decreasing amount of cholic acid in an aqueous solution. The USP Dissolution Apparatus 2 (paddle) Ph. Eur. 2.9.3 was used.

An amount of formulation A, B or C corresponding to 250 mg cholestyramine was added to a vessel containing 250 mL 0.1 M hydrochloric acid solution (pH 1) and the contents were stirred at 75 rpm for 2 hours. 250 mL of a solution of cholic acid in potassium hydroxide/potassium phosphate buffer solution was then added to the vessel, giving a buffered solution of cholic acid (0.192 mg/mL) with pH 6.8. After 1 minute of mixing, a first sample was removed. The pH was thereafter verified and if necessary adjusted to 6.8 by addition of the appropriate amount of 0.1 M potassium hydroxide solution. The solution was thereafter mixed for an additional 6 hours. Samples of the solution were withdrawn at different time points and analysed for cholic acid by HPLC using a Thermo Hypersil Gold column, 50 mm×2.1 mm, particle size 1.9 µm; column temperature 60° C.; mobile phase 30:70 acetonitrile:phosphate buffer (pH 3.0); flow rate 0.75 mL/min. 5 replicate samples were analysed for each formulation and the average values were calculated.

Figure 1:
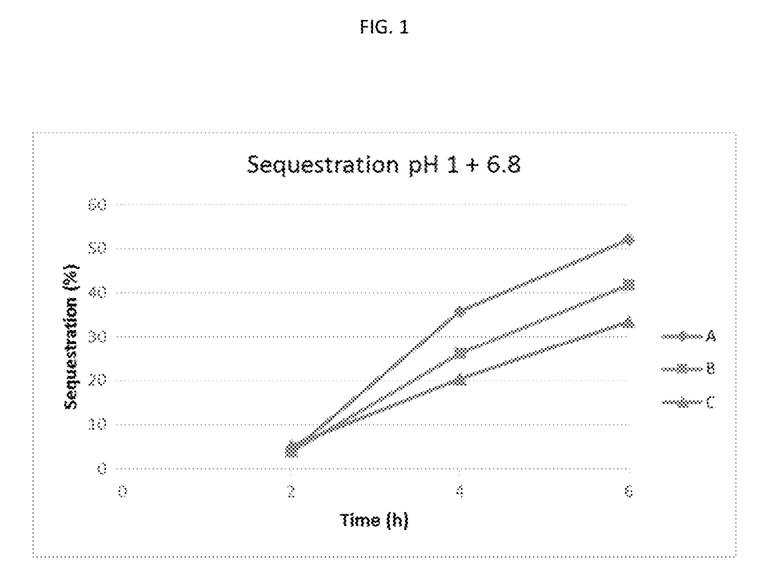
FIG. 1 shows the sequestration profiles for formulations A, B, and C in an assay simulating the stomach (2 hours at pH 1) and the small intestine (4 hours at pH 6.8).

The results are shown in FIG. 1. Formulations A, B and C gave 52%, 42% and 34% sequestration, respectively, after 2 hours at pH 1 followed by 4 hours at pH 6.8.

Example 2

Determination of the Sequestering Capacity of Cholestyramine Under Conditions Representative of the Human Colon The bile acid sequestering capacity of three different doses of cholestyramine was studied in the Simulator of the Human Intestinal Microbial Ecosystem (SHIME®). Cholestyramine (16 mg, 41 mg and 65 mg) were added to colon liquid media comprising a SHIME® matrix representative for the human proximal colon, in the presence of a 4 mM-dose of a 40:40:20 (w/w) mixture of CA, CDCA and DCA. A parallel control experiment was conducted in which no cholestyramine was added. Each experiment was conducted in triplicate to account for possible variability.

Conditions for HPLC Analysis

The bile salts cholic acid (CA), chenodeoxycholic acid (CDCA) and deoxycholic acid (DCA) were detected and quantified by HPLC, using a Hitachi Chromaster HPLC equipped with a UV-Vis detector. The three compounds (CA, CDCA, and DCA) were separated by a reversed-phase C18 column (Hydro-RP, 4 µm, 80 Å, 250×4.6 mm, Synergi). The separation was performed under isocratic conditions at room temperature, using a 80:20 (v:v) mixture of methanol and phosphate buffer (0.01 M $KH_2PO_4$, 0.02 M $NaH_2PO_4$ at pH 3) as the mobile phase. The analysis was performed at 0.7 mL/min during 23 minutes and the bile salts were detected at 210 nm. The injection volume was set at 20 µL for stomach and small intestine samples and 50 µL for colon samples.

Calibration of the Standards in the SHIME® Matrix

To define the calibration curve, five different concentration levels (20 to 1500 mg/L) of CA, CDCA, and DCA standard solutions were prepared in a mixture of basal medium and SHIME® inoculum (90:10, v:v) and centrifuged during 2 min at 5000 g. 500 µL of the supernatant was mixed with 500 µL of a 80:20 (v:v) mixture of methanol and phosphate buffer, vigorously vortexed, filtered through a 0.2 µm PTFE filter and injected in the HPLC system. The calibration curves were constructed by plotting the area of each bile salt versus the concentration of the standard solutions. The coefficients of determination ($R^2$) obtained were higher than 0.99.

Sequestering Assay

Colonic incubations were performed for 4 h, at 37° C., under anaerobic conditions and with an in vitro adapted microbial community representative of the microbiota present in the human proximal colon. Samples were collected every 30 minutes (a total of 8 samples/incubation) and the concentration of free bile salts was assessed by means of HPLC. One mL of each sample was centrifuged for 2 min at 5000 g. 500 µL of the supernatant was mixed with 500 µL of a 80:20 (v:v) mixture of methanol and phosphate buffer, vigorously vortexed, filtered through a 0.2 µm PTFE filter and injected in the HPLC system. The concentrations of bile salts in the samples were calculated using the previously obtained calibration curves.

Figure 2:
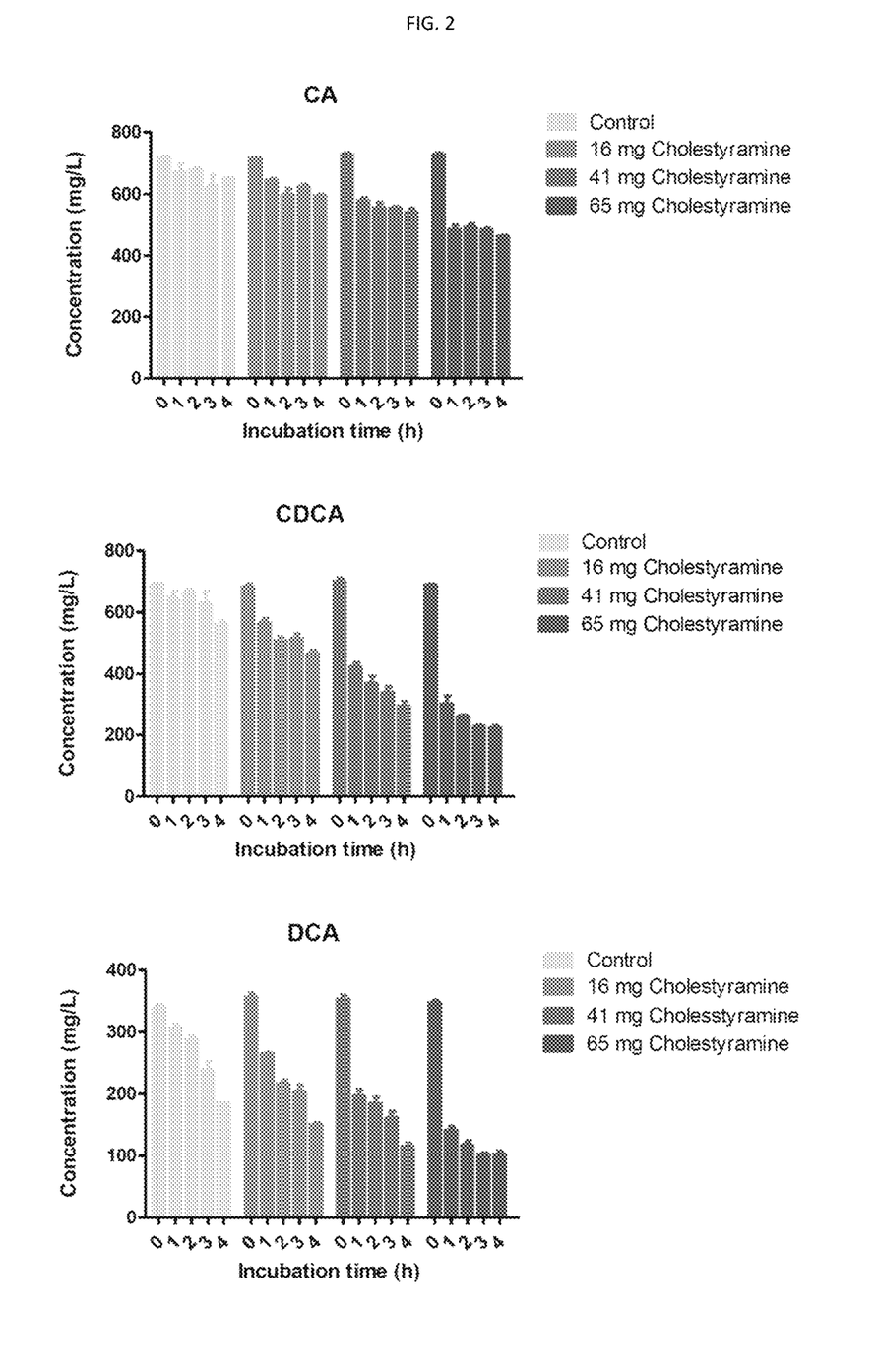
FIG. 2 shows the cholic acid (CA), chenodeoxycholic acid (CDCA) and deoxycholic acid (DCA) concentrations (mg/L) vs. incubation time (h) under conditions representative for the human colon, in experiments using three different amounts of cholestyramine. The results for a control experiment without cholestyramine are also shown.

The results of the analyses for CA, CDCA and DCA are shown in the graphs in FIG. 2. The graphs only include the samples taken at 0 hours and after 1, 2, 3 and 4 hours of incubation.

Example 3

Determination of the Sequestering Capacity of Cholestyramine Formulations Under Conditions Representative of the Stomach, Small Intestine and the Ascending Colon The bile acid sequestering capacity of four different colon release formulations of cholestyramine was studied in the Simulator of the Human Intestinal Microbial Ecosystem (SHIME®). The simulator was adapted to evaluate the capacity of binding bile salts under physiological conditions representative of fasted stomach, small intestine and proximal colon. A 40:40:20 (w/w) mixture of cholic acid (CA), chenodeoxycholic acid (CDCA) and deoxycholic acid (DCA) was used as a representative mixture of human bile salts.

A comparative experiment to which pure (unformulated) cholestyramine powder was added was also conducted. A control experiment to which no cholestyramine was added was conducted in order to monitor the degradation of the bile salts under the colonic conditions used in the assay.

Each experiment was performed in triplicate to account for biological variation.

Fasted stomach Four different cholestyramine formulations containing 91 mg of cholestyramine, or pure (naked) cholestyramine (91 mg) were dosed to 14 mL stomach liquid medium (pH 1.8) containing water, NaCl (5.984 g/L), pepsin (1 g/L) and mucin (4 g/L). The digests were incubated for 1 hour at 37° C.

Small Intestine

After one hour of stomach incubation, 5.6 mL pancreatic juice (pH 6.8) containing the defined 40:40:20 mixture of bile salts (46.7 mM), pancreatin (0.9 g/L) and $NaHCO_3$ (12.5 g/L) was added. The small intestine digests were incubated for 2 hours at 37° C. and samples were taken after 0, 60 and 120 minutes.

Proximal Colon

After two hours of small intestine incubation, 42 mL of a full SHIME® matrix (pH 6) originated from the ascending colon of a SHIME® system was added. The colon digests were incubated for 24 hours at 37° C. and samples were collected every 30 minutes for the first 6 hours and a last sample at 24 hours.

The concentration of free bile salts in the samples was assessed by means of the HPLC method described above. The matrix representative for the human proximal colon incubations contained a mixture of (degraded) bile salts originating from BD Difco™ Oxgall. A higher quantity of free bile salts could therefore be expected in the colon samples. The values of the background (i.e. blank sample where no mix of bile salts was added) were therefore subtracted from each sample in order to take into account the 'baseline' of free bile salts present in the matrix.

Figure 3:
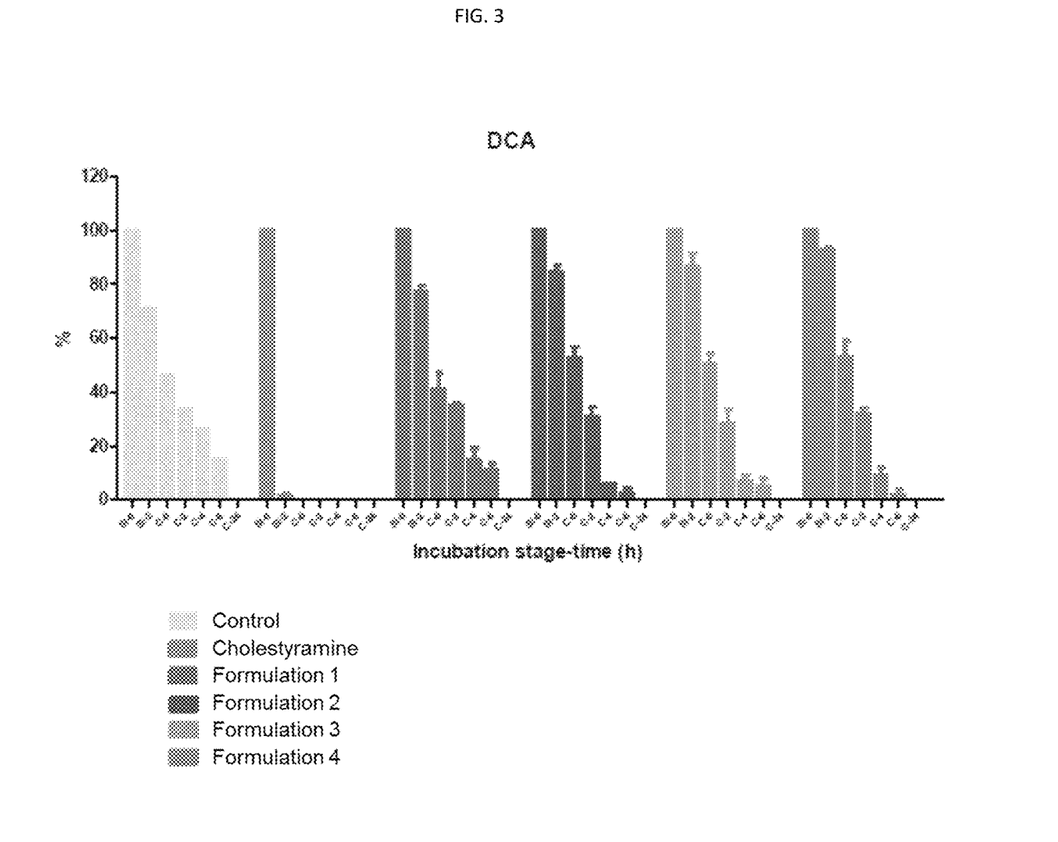
FIG. 3 shows the % reduction of the concentration of deoxycholic acid compared to the concentration added at the start of the experiment for four different colon release formulations comprising cholestyramine. The results for a comparative experiment using pure cholestyramine powder and a control experiment without cholestyramine are also shown.

The % reduction of the concentration of DCA compared to the concentration added at the start of the experiment is shown in the graph in FIG. 3. The graph includes the samples taken after 0 hours and 2 hours of small intestinal (SI) incubation, and after 0, 2, 4, 6 and 24 hours of colonic (C) incubation.

The invention claimed is:

1. An in vitro method for determining the adsorbing capacity of an adsorbent having limited solubility, under conditions simulating the mammalian gastrointestinal tract, wherein the method comprises the steps of:
    a) providing a liquid medium representative of at least one region of the gastrointestinal tract;
    b) adding to said liquid medium defined amounts of an adsorbent and a marker compound; and
    c) incubating the mixture obtained in step (b) and measuring the amount of free marker compound in said mixture.

2. The method according to claim 1, wherein the adsorbent has less than 5% solubility in aqueous conditions.

3. The method according to claim 1, wherein the conditions simulating the mammalian gastrointestinal tract are conditions simulating the stomach and the small intestine.

4. The method according to claim 1, wherein the conditions simulating the mammalian gastrointestinal tract are conditions simulating the small intestine and the colon.

5. The method according to claim 1, wherein the conditions simulating the mammalian gastrointestinal tract are conditions simulating the stomach, the small intestine and the colon.

6. The method according to claim 1, wherein the liquid medium is a stomach liquid medium comprising pepsin and mucin.

7. The method according to claim 1, wherein the liquid medium is a small intestine liquid medium comprising bile acids or salts.

8. The method according to claim 1, wherein the liquid medium is a colon liquid medium comprising a stable microbial community representative of the colon.

9. The method according to claim 1, wherein the adsorbent is a bile acid sequestrant.

10. The method according to claim 9, wherein the bile acid sequestrant is cholestyramine.

11. The method according to claim 10, wherein the marker compound is a bile acid.

12. The method according to claim 11, wherein the marker compound is a mixture of bile acids.

13. The method according to claim 12, wherein the mixture of bile acids comprises cholic acid (CA), chenodeoxycholic acid (CDCA) and deoxycholic acid (DCA).

14. The method according to claim 13, wherein the ratio between CA, CDCA and DCA is 40:40:20 (w/w).

15. An in vitro method for determining the adsorbing capacity of an adsorbent having limited solubility, under conditions simulating the mammalian gastrointestinal tract, wherein the method comprises the steps of:
    a) providing a liquid medium representative of the stomach;
    b) adding to said liquid medium a defined amount of an adsorbent;
    c) incubating the mixture obtained in step (b);
    d) converting the mixture of step c) to a medium representative of the small intestine;
    e) adding a defined amount of a marker compound to the mixture of step d);
    f) incubating the mixture obtained in step (e) and measuring the amount of free marker compound in said mixture;
    g) converting the mixture of step f) to a medium representative of the colon; and
    h) incubating the mixture obtained in step (g) and measuring the amount of free marker compound in said mixture.

16. The method according to claim 15, wherein the stomach liquid medium comprises pepsin and mucin.

17. The method according to claim 15, wherein the small intestine liquid medium comprises bile acids or salts.

18. The method according to claim 15, wherein the colon liquid medium comprises a stable microbial community representative of the colon.

19. The method according to claim 15, wherein the adsorbent is a bile acid sequestrant.

20. The method according to claim 19, wherein the bile acid sequestrant is cholestyramine.

21. The method according to claim 19, wherein the marker compound is a bile acid.

22. The method according to claim 21, wherein the marker compound is a mixture of bile acids.

23. The method according to claim 22, wherein the mixture of bile acids comprises cholic acid (CA), chenodeoxycholic acid (CDCA) and deoxycholic acid (DCA).

24. The method according to claim 23, wherein the ratio between CA, CDCA and DCA is 40:40:20 (w/w).

* * * * *